(12) United States Patent
Chen et al.

(10) Patent No.: US 7,629,131 B2
(45) Date of Patent: Dec. 8, 2009

(54) RABBIT MONOCLONAL ANTIBODIES AGAINST MOUSE/HUMAN ID3 PROTEINS

(75) Inventors: Jung-Shou Chen, Foster City, CA (US); William A. Garland, San Clemente, CA (US)

(73) Assignees: Biocheck, Inc., Foster City, CA (US); Angiogenex, Inc., New York, NY (US)

( * ) Notice: Subject to any disclaimer, the term of this patent is extended or adjusted under 35 U.S.C. 154(b) by 334 days.

(21) Appl. No.: 11/657,426

(22) Filed: Jan. 23, 2007

(65) Prior Publication Data

US 2007/0178531 A1    Aug. 2, 2007

Related U.S. Application Data

(60) Provisional application No. 60/763,076, filed on Jan. 27, 2006.

(51) Int. Cl.
*G01N 33/53* (2006.01)
*C07K 16/28* (2006.01)

(52) U.S. Cl. .................... 435/7.1; 530/388.24

(58) Field of Classification Search ............ None
See application file for complete search history.

(56) References Cited

U.S. PATENT DOCUMENTS

| | | | | |
|---|---|---|---|---|
| 5,654,188 A | * | 8/1997 | Ellmeier et al. | 435/368 |
| 5,675,063 A | * | 10/1997 | Knight | 800/14 |
| 5,939,272 A | * | 8/1999 | Buechler et al. | 435/7.1 |
| 7,370,021 B2 | * | 5/2008 | Reeve et al. | 706/16 |
| 2003/0023995 A1 | | 1/2003 | Benezra | |
| 2003/0152921 A1 | | 8/2003 | Edwards et al. | |

OTHER PUBLICATIONS

Forrest et al., "Intron Retention Generates a Novel Id3 Isoform That Inhibits Vascular Lesion Formation", The Journal of Biological Chemistry, Jul. 2004, vol. 279, No. 31, pp. 32897-32903, see abstact and p. 32899.

Matsumura et al., "Vascular Injury Induces Posttranscriptional Regulation of the Id3 Gene: Cloning of a Novel Id3 Isoform Expressed During Vascular Lesion Formation in Rat and Human Atheroschlerosis", Arteriosclerosis, Thrombosis, and Vascular Biology, May 2001, vol. 21, pp. 752-758.

* cited by examiner

*Primary Examiner*—Maher M Haddad
(74) *Attorney, Agent, or Firm*—Howrey LLP

(57) ABSTRACT

The present invention relates to a rabbit monoclonal antibody that binds to human Id3 protein and/or mouse Id3 protein with high specificity and high affinity. The antibody has a binding constant, measured with respect to human Id3 protein or mouse Id3, of greater than $1 \times 10^8$/molar. The antibody has no substantial cross-reactivity to other family Id proteins such as Id1, Id2, or Id4, or other endogenous proteins present in the cells that express Id3 protein. The specificity and high affinity of the rabbit monoclonal antibodies of the present invention allows sensitive and specific detection and/or quantitation of human or mouse Id3 protein in biological samples. The antibodies are useful in immunochemical-based assays such as ELISA, western blot, and immunohistochemical staining.

13 Claims, 3 Drawing Sheets
(1 of 3 Drawing Sheet(s) Filed in Color)

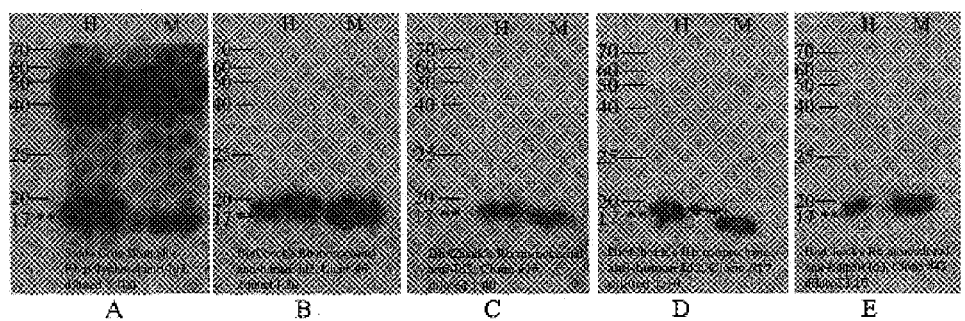
FIG. 1.1
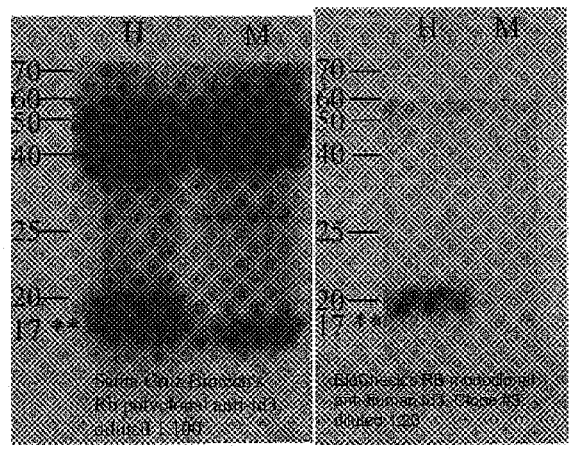
FIG. 1.2

US 7,629,131 B2

RABBIT MONOCLONAL ANTIBODIES AGAINST MOUSE/HUMAN ID3 PROTEINS

The present invention claims the benefit of U.S. Provisional Application No. 60/763,076, filed Jan. 27, 2006, which is incorporated herein by reference in its entirety.

FIELD OF THE INVENTION

The field of this invention relates to rabbit monoclonal antibodies against human Id3 protein and/or mouse Id3 protein and the use of these antibodies in immunochemical-based assays to detect and/or quantitate Id3 proteins in biological samples.

BACKGROUND OF THE INVENTION

Inhibitor of differentiation (Id) proteins are transcriptional regulators implicated in diverse developmental, physiologic and pathologic processes such as cancer and atherogenesis, and the Id3 genes and proteins are an important member of this class [Lim et al., Acta Pharmacol Sin; 26:1409-20 (2005)].

Id genes are widely expressed in the animal kingdom from humans to zebra fish [Dickmeis et al., Mech Dev; 113:99-102 (2002)]. Four Id genes, Id1-Id4, have been identified in humans and in rodents. A homologous Id-like gene, extramacrochaetae has been identified in drosophila [Campuzano et al., Oncogene; 20:8299-307 (2001)]. The name, inhibitor of differentiation, derives from the property of the Id proteins to diminish the differentiation of a variety of cells by inhibiting the DNA binding activity of many transcription factors that regulate expression of cell-type specific genes.

The Id proteins are small proteins of approximately 13 kDa-20 kDa. All four Id proteins contain a modestly conserved helix-loop-helix (HLH) structural motif in the middle of the protein, but are otherwise divergent in sequences. The four Id proteins constitute one subclass (Class V) of the large family of HLH transcriptional regulators. Unlike other HLH proteins that can bind to DNA as homodimers or heterodimers, the Id proteins lack the basic amino acid domain needed for DNA binding. Instead, they function primarily by forming heterodimers with the "ubiquitous" Class I HLH proteins known as E-proteins. This dimerization prevents the E-proteins from interacting with each other and with cell-type specific Class II HLH proteins by inhibiting their binding to DNA and repressing their ability to modulate gene expression. This modulation can include both inhibition and stimulation of gene expression. For example, some class I bHLH proteins repress transcription and with these repressor proteins sequestration could ameliorate their inhibitory effects and lead to increased gene expression. For other transcription factors such as ETS, SREBP-1, Pax5, etc., Id proteins interact and inhibit. Certain individual members of the Id family proteins interact selectively with specific proteins. Individual Id proteins might interact selectively with proteins not recognized by other Id family members. For example, Id1 is the only Id protein shown to bind the proteasomal protein S5a [Anand et al., J Biol Chem; 272:19140-51 (1997)], and as previously mentioned only Id2 binds to the tumor suppressor retinoblastoma protein Rb and interferes with the ability of hypophosphorylated Rb to suppress cell proliferation when both are ectopically expressed [Lasorella et al., Mol Cell Biol; 16:2570-8 (1996)].

The Id family proteins have been extensively reviewed [Sidker et al., Cancer Cell; 3:525-30 (2003), Benezra et al., Oncogene; 20:8334-41 (2001), Lasorella et al., Oncogene; 20:8326-33 (2001), Yokota et al., J. Cell Physiol; 190:21-28 (2002), Ruzinova et al., Trends Cell Biol; 13:410-18 (2003)]. Most of these reviews have dealt with the Id proteins as a group and concentrated primarily on the potential biological functions of the Id proteins. Relatively less attention has been devoted to reviewing the molecular mechanisms that regulate the expression and function of individual Id genes and proteins.

The Id3 gene was first identified as a serum-inducible immediate early gene in an established murine fibroblastic cell line [Christy et al., Proc Natl Acad Sci USA; 88:1815-27 (1991)]. Subsequent studies have documented their involvement in various biological processes, including T and B cell development, skeletal muscle differentiation [Atherton et al., Cell Growth Differ; 7:1059-66 (1996), Melnikova et al., Cell Growth Differ; 7:1067-79 (1996)], vascular smooth muscle cell proliferation [Forrest et al., J Biol Chem; 279:32897-903 (2004), Deed et al., FEBS Lett; 393:113-6 (1996)], embryonic neurogenesis, osteogenesis [Maeda et al., J Cell Biochem; 93:337-44 (2004)], and tumor-induced angiogenesis. Expression and function of the protein is under many complex layers of regulation and, therefore, could provide rich targets for therapeutic interventions.

Several studies have characterized the expression of Id3 at either the mRNA or the protein level. A wide range of techniques have been utilized, including Northern, in situ hybridization, reverse transcription with polymerase chain reaction, various genome expression profiling assays, Western immunoblots and immunocytochemical staining procedures. Like other Id genes, the expression of Id3 is dynamically regulated during embryonic development. The general expression level is high at the early embryonic ages, but progressively declines as the embryo develops [Ellmeier et al., Dev Dyn; 203:163-73 (1995)]. Id3 is widely expressed throughout the embryo proper. Its expression is readily detectable within regions that are undergoing active morphogenesis [Jen et al., Dev Dyn; 207:235-52 (1996)], but can also be detected in some undifferentiated tissues.

Id3 is expressed by many, but not all, cells indicating that its regulation is likely to involve both ubiquitous as well as cell-type specific regulatory mechanisms. Perturbation of Id3 expression has been correlated with a variety of disease states and pathologic situations, including cancer, aging, atherosclerosis, muscle atrophy, and inflammation. Conversely, altered expression of Id3 has been detected during the regenerative process following tissue injury.

It is generally believed that members of the Id gene family behave like oncogenes. Overexpression of one or more Id genes has been detected in various cancers. The situation with Id3 is consistent in most part with this generalization [Wilson et al., Cancer Res; 61:8803-10 (2001), Langlands et al., Cancer Res; 60:5929-33 (2000)], but there are some exceptions. In certain neurological tumors, Id3 upregulation is observed not only in the tumors themselves but also in the vascular tissues surrounding the tumors [Vandeputte et al., Glia; 38:329-38 (2002)]. In contrast, expression is reduced in papillary thyroid carcinoma [Deleu et al., Exp Cell Res; 279:62-70 (2002)] and ovarian carcinomas [Arnold et al., Br J Cancer; 84:352-9 (2001)], and either increased [Sablitzky et al., Cell Growth Differ; 9:1015-24 (1998)] or absent [Albanese et al., Diagn Mol Pathol; 10:248-54 (2001)] in seminoma. The expression pattern is even more complex during the development of liver diseases and liver cancer. Id3 expression is low in normal liver, increases with the progression of liver diseases from chronic hepatitis to liver cirrhosis and is expressed at high levels in well-differentiated hepatocarcinomas, but not in the more advanced de-differentiated tumors [Damdinsuren et al., Int J Oncol; 26:319-27 (2005)].

Id3 expression level also changes in inflammatory and atherogenic processes. Id gene expression is upregulated in reactive astrocytes activated as part of the inflammatory process following spinal cord injury [Tzeng et al., Glia; 26:139-52 (1999)]. Id3 expression is also altered in vascular smooth muscle cells (VSMC) during atherogenesis. It is expressed at low level in normal vessels of the carotid artery, but is increased within 3 days of balloon injury and remains high through 14 days post injury. This is accompanied by the appearance of a novel differentially spliced Id3 transcript.

The inhibitor of differentiation transcription factor Id3 is implicated in numerous, diverse developmental, physiologic and pathophysiologic processes. Although some overlap with the other Id genes and protein is apparent, Id3 has a distinct expression, location and activity profile. Many of the biologic processes affected by Id3 are important to significant human disease such as cancer and atherogenesis as well as inappropriate immunity such as after tissue and/or organ transplantation. In addition, Id3 itself is regulated by many biologically important systems so that the amount of Id3 present in a particular matrix represents an integration of many important processes many of which are indicative of pathology. Methods to measure Id3 in biologic matrices to establish the Id3 status of the biologic test material are important for diagnostic, prognostic or research purposes. Such methods require an excellent sensitivity because Id3 is active at very low concentrations [Langlands et al., J Biol Chem; 272: 19785-93 (1997)]. Such methods also require a high degree of specificity with respect to other endogenous materials in the biologic matrices and other Id proteins.

Production of monoclonal antibodies specific to Id3 is difficult because of the relatively low molecular weight (about 17 kDa) and common structural homology among the Id proteins. Commercial rabbit polyclonal anti-mouse/human Id3 antibody (Santa Cruz Biotechnology, Santa Cruz, Calif.) does not have desired properties because it has cross-reactivity with other proteins in a biological sample and it does not have high affinity to Id3. The undesired cross-reactivity and low binding affinity make the commercial antibodies unsuitable for use in immunoassays to detect Id3. It is difficult to prepare polyclonal antibodies specific only to human Id3, with no cross-reactivity to mouse Id3; or specific only to mouse Id3, with no cross-reactivity to human Id3 because of the homology between mouse Id3 and human Id3.

There is a need for antibodies specific for Id3, which do not substantially cross-react with other endogenous proteins in a biological sample or those within the Id family proteins such as Id1, Id2, and Id4. There is also a need for antibodies that have high binding constant to Id3 such that they are sensitive to detect or quantitate Id3 in biological samples. There is further a need for antibodies that are specific only to mouse Id3 or specific only to human Id3 with no substantial cross-reactivity between the two species, for research purpose.

SUMMARY OF THE INVENTION

The present invention is directed to a rabbit monoclonal antibody that binds to human Id3 and/or mouse Id3 protein with high specificity and high affinity. The antibody has a binding constant, measured with respect to human Id3 protein or mouse Id3 protein, of greater than $1\times10^8$/molar, preferably $1\times10^9$, more preferably $1\times10^{10}$, more preferably $1\times10^{11}$, more preferably $1\times10^{12}$, and most preferably $1\times10^{13}$. The antibody has no substantial cross-reactivity to other family Id proteins such as Id1, Id2, or Id4, or other endogenous proteins present in the cells that express Id3 protein.

In one embodiment of the invention, the rabbit monoclonal antibody only had reactivity toward human Id3 protein and had no substantial reactivity toward mouse Id3 protein. In another embodiment of the invention, the rabbit monoclonal antibodies only have reactivity toward mouse Id3 protein and have no substantial reactivity toward human Id3 protein. In a further embodiment of the invention, the rabbit monoclonal antibodies have substantial reactivity toward both human Id3 and mouse Id3 protein.

The specificity and high affinity of the rabbit monoclonal antibodies of the present invention allows sensitive and specific detection and quantitation of Id3 protein in biological samples. The antibodies are useful in immunochemical-based assays such as ELISA, western blot, and immunohistochemical staining. The antibodies provide a tool for sensitive and accurate detection of a disease, which results in the overproduction of Id3 such as breast cancer and other cancers. The antibodies also provide a tool for assess Id3 levels in various experimental biologic test systems.

BRIEF DESCRIPTION OF THE DRAWINGS

This application file contains at least one drawing executed in color. Copies of this patent or patent application publication with color drawing(s) will be provided by the Office upon request and payment of the necessary fee.

FIG. 1.1 shows Western blots analyses. Lanes marked "H" were extracts from Hela cells that express human Id3. Lanes marked "M" were extracts from 10T1/2 mouse embryonic fibroblast cells that express mouse Id3. Santa Cruz Biotechnology's rabbit polyclonal anti-mouse/human Id3 was used to develop blot A. Rabbit monoclonal anti-mouse/human Id3, clone #BCH-4/#6-1, clone #BCH-4/#16-1, clone #BCH-4/#17-3, and clone #BCH-4/#42-1, of this invention were used to develop blot B, C, D, and E accordingly. In these blots the molecular weight markers are kDa and the MW of Id3, ~17 kDa, is designated with **.

FIG. 1.2 shows Western blots analyses. Lanes marked "H" were extracts from Hela cells that express human Id3. Lanes marked "M" were extracts from 10T1/2 mouse embryonic fibroblast cells that express mouse Id3. Santa Cruz Biotechnology's rabbit polyclonal anti-mouse/human Id3 was used to develop blot A. The rabbit monoclonal anti-human Id3, clone #BCH-4/#3-3, of this invention was used to develop blot B. In these blots the molecular weight markers are kDa and the MW of Id3, ~17 kDa, is designated with **.

FIG. 2A shows the results of a negative control of purified rabbit IgG. FIG. 2B shows the results of rabbit monoclonal anti-mouse/human Id3, Clone #BCH-4/#6-1. FIG. 2C shows the results of rabbit monoclonal anti-mouse/human Id3, Clone #BCH-4/#16-1. FIG. 2D shows the results of rabbit monoclonal anti-mouse/human Id3, Clone #BCH-4/#17-3. FIG. 2E shows the results of rabbit monoclonal anti-mouse/human Id3, Clone #BCH-4/#42-1.

DETAILED DESCRIPTION OF THE INVENTION

Definitions

Figure 2:
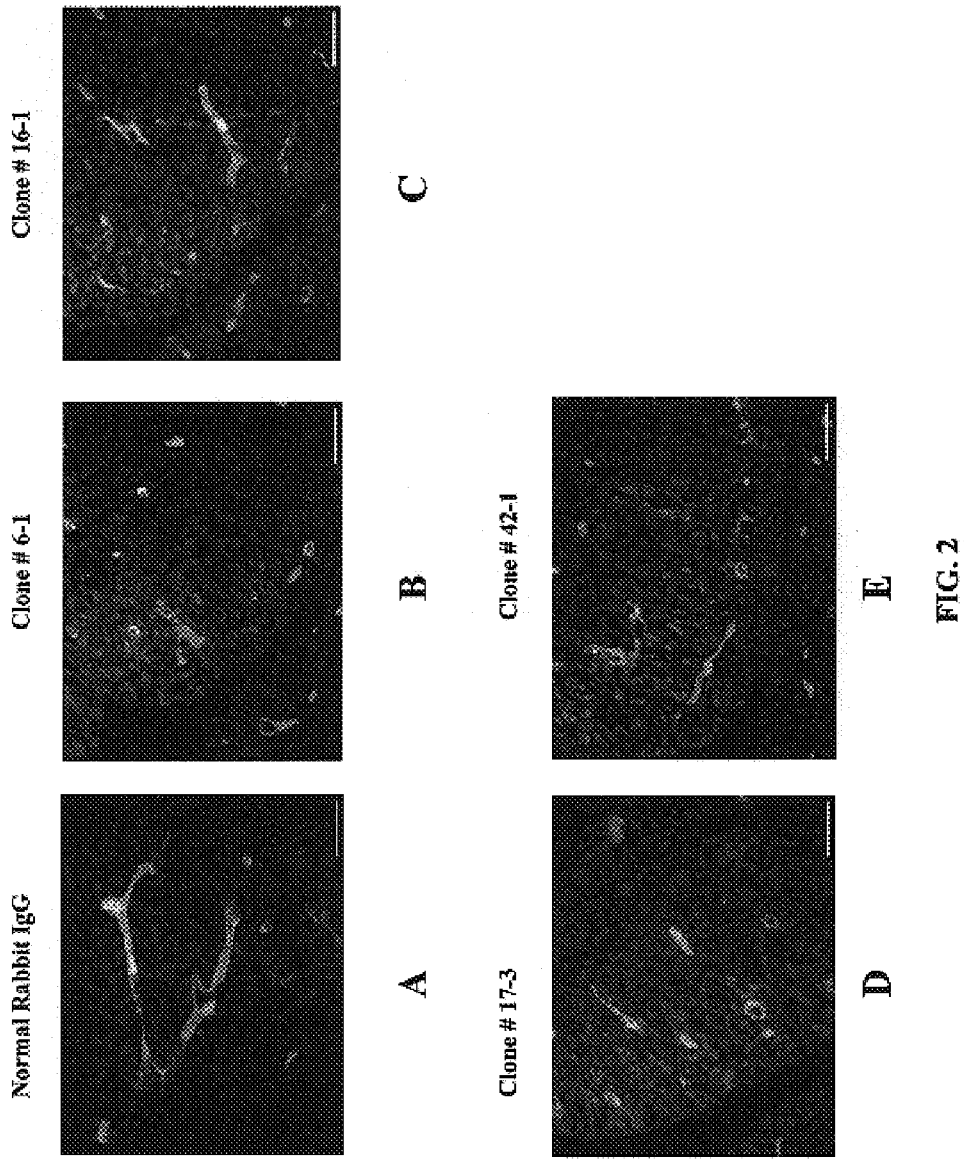
FIGS. 2A-2E show the fluorescence microscopy immunohistochemistry staining results by using the rabbit monoclonal anti-Id3 of this invention to detect mouse Id3 in embryonic mouse brain sections (E13.5).

When present, unless otherwise specified, the following terms are generally defined as, but are not limited to, the following:

The term "antibody" refers to a specific protein binding partner for an antigen and is any substance, or group of substances, which has a specific binding affinity for an antigen to the exclusion of other substances. The generic term antibody includes polyclonal antibodies, monoclonal antibodies and antibody fragments (e.g. Fab' or (Fab')$_2$) of polyclonal antibodies or monoclonal antibodies. The generic term monoclonal antibodies include antibody fragments (e.g. Fab' or (Fab')$_2$) of monoclonal antibodies.

The term "affinity" refers to the strength with which an antibody molecule binds an epitope (antigenic determinant). Affinity can be quantified by determining an association constant.

The term "binding constant" or "equilibrium association constant" of an antibody refers to the value of [Ab–Ag]/[Ab][Ag] at equilibrium, where [Ab–Ag] is the concentration of antibody-antigen complexes, [Ab] is the unbound (free) concentration of antibody, and [Ag] is the unbound (free) concentration of antigen. The higher the binding constant, the higher the affinity of the antibody binds to the antigen. Equilibrium association constant is reciprocal of equilibrium dissociation constant.

The term "biological sample" refers to a sample from a living thing or formerly living thing. Such living things include, but are not limited to, human beings, mice, monkeys, rats, rabbits, horses, goats, and other animals. Such samples include, but are not limited to, blood, serum, plasma, urine, cells, organs, tissues, bone, bone marrow, lymph, lymph nodes, synovial tissue, chondrocytes, synovial macrophages, endothelial cells, and skin. Preferred biological samples for detecting Id3 are mouse or human tissue samples, or patient samples such as blood and plasma. The term also includes cell cultures derived from living things or formerly living things.

The term "conjugate" refers to any substance formed from the joining together of two parts.

The term "diagnostic" test, procedure, or instrument refers to a test, procedure, or instrument used to identify the nature or cause of an illness, disorder or problem.

The term "drug screening" refers to an assay used to determine the properties of a drug or drug candidate with respect to efficacy or safety or characteristics that impact on the safety or efficacy of a drug or drug candidate. These assays permit efficient prioritization and comparison of drugs or drug candidates The terms "immunogen" and "immunogenic" refer to substances capable of eliciting, producing, or generating an immune response in an organism.

The term "immunogenic carrier," refers to an immunogenic substance, commonly a protein, that can join with an antigen, in this case Id3, thereby enabling the Id3 to induce an immune response and elicit the production of antibodies that can bind specifically with the Id3. The immunogenic substances include proteins, glycoproteins, complex polyamino-polysaccharides, particles, and nucleic acids that are recognized as foreign and thereby elicit an immunologic response from the host. The polyamino-polysaccharides may be prepared from polysaccharides using any of the conventional means known for this preparation.

Various protein types may be employed as immunogenic carriers. Illustrative proteins include bovine serum albumin (BSA), keyhole limpet hemocyanin (KLH), egg ovalbumin, bovine thyroglobulin (BTG), yellow fluorescent protein (YFP), or glutathione S-transferase (GST). Alternatively, synthetic polyamino acids may be utilized in place of proteins.

Immunogenic carriers can also include poly amino-polysaccharides, which are high molecular weight polymer built up by repeated condensations of monosaccharides. Examples of polysaccharides are starches, glycogen, cellulose, carbohydrate gums such as gum arabic, agar, and so forth. The polysaccharide may also contain polyamino acid residues and/or lipid residues. The immunogenic carrier can also be a polynucleic acids either alone or conjugated to one of the above mentioned polyamino acids or polysaccharides.

The term "label," or "a reporter molecule," refers to any molecule that produces, or can be induced to produce, a detectable signal. Non-limiting examples of reporter molecules include radioactive isotopes, enzymes, enzyme fragments, enzyme substrates, enzyme inhibitors, coenzymes, catalysts, fluorophores, dyes, chemiluminescers, luminescers, or sensitizers; a non-magnetic or magnetic particle, a solid support, a liposome, a ligand, or a receptor. Preferred reporter molecules are enzymes such as horseradish peroxidase, alkaline phosphatase, or β-galactosidase.

The term "no substantial cross-reactivity," in general refers to cross-reactivity of <10%, preferably <5%, more preferably <2%, more preferably <1%, and most preferably <0.1%.

The term "prognostic" test refers to a test indicating likely course of an illness, disorder or problem.

The term "specificity" of an antibody refers to the antibody's ability to discriminate between two different epitopes.

The present invention is directed to rabbit monoclonal antibodies that bind to human Id3 protein and/or mouse Id3 protein. The rabbit monoclonal antibodies of the present invention are substantially specific for Id3 and do not substantially cross-react with other proteins such as other proteins of the Id family and other endogenous proteins in a biological sample. The antibodies are sufficiently sensitive in detecting and measuring Id3 at concentrations that are biologically significant in biological samples.

The rabbit monoclonal antibodies of the present invention have a binding constant, measured with respect to human Id3 protein or mouse Id3 protein, in general greater than $1 \times 10^8$, more preferably $1 \times 10^9$, more preferably $1 \times 10^{10}$, more preferably $1 \times 10^{11}$, more preferably $1 \times 10^{12}$, and most preferably $1 \times 10^{13}$. The high binding constant of the antibodies indicates high affinity of the antibodies to human Id3, and provides a high sensitivity for detection of Id3 protein.

The rabbit monoclonal antibodies of the present invention have no substantial cross-reactivity to other proteins of the Id family, e.g., Id1, Id2, and Id4 proteins, particularly Id1 and Id2; thus allows it to specifically detect the presence of Id3, instead of other Id proteins. The rabbit monoclonal antibodies of the present invention further have no substantial cross-reactivity to other endogenous proteins that are present in the cells that express Id3 protein. "No substantial cross-reactivity," as used herein, in general refers to <10%, preferably <5%, more preferably <2%, more preferably <1%, and most preferably <0.1%.

The specificity and high affinity of the rabbit monoclonal antibodies of the present invention allows sensitive and specific detection and quantitation of Id3 protein, thus providing a tool for sensitive and accurate diagnosis of a disease that cause overproduction of Id3 such as breast cancer and other cancers. The antibodies are also useful in immunochemical-based assays to assess Id3 levels in various experimental biologic test systems, for example, systems that measure the ability of test chemicals to modulate Id3 protein concentration, Id3 protein activity, and Id3 gene expression.

Human Id3 protein and mouse Id3 protein have about 95% homology. The DNA sequence (SEQ ID NO:1) of human Id3 protein is as follows:

```
ATGAAGGCGC TGAGCCCGGT GCGCGGCTGC TACGAGGCGG

TGTGCTGCCT GTCGGAACGC AGTCTGGCCA TCGCCCGGGG

CCGAGGGAAG GGCCCGGCAG CTGAGGAGCC GCTGAGCTTG

CTGGACGACA TGAACCACTG CTACTCCCGC CTGCGGGAAC

TGGTACCCGG AGTCCCGAGA GGCACTCAGC TTAGCCAGGT

GGAAATCCTA CAGCGCGTCA TCGACTACAT TCTCGACCTG

CAGGTAGTCC TGGCCGAGCC AGCCCCTGGA CCCCCTGATG

GCCCCCACCT TCCCATCCAG ACAGCCGAGC TCGCTCCGGA

ACTTGTCATC TCCAACGACA AAAGGAGCTT TTGCCACTGA
```

The amino acid sequence (SEQ ID NO:2) for human Id3 protein is as follows:

```
MKALSPVRGC YEAVCCLSER SLAIARGRGK GPAAEEPLSL

LDDMNHCYSR LRELVPGVPR GTQLSQVEIL QRVIDYILDL

QVVLAEPAPG PPDGPHLPIQ TAELAPELVI SNDKRSFCH
```

The DNA sequence for mouse Id3 (SEQ ID NO:3) protein is as follows:

```
ATGAAGGCGC TGAGCCCGGT GCGCGGCTGC TACGAGGCGG

TGTGCTGCCT GTCGGAACGT AGCCTGGCCA TTGCGCGAGG

CCGCGGTAAG AGCCCGTCGA CCGAGGAGCC TCTTAGCCTC

TTGGACGACA TGAACCACTG CTACTCGCGC CTGCGGGAAC

TGGTGCCGGG AGTCCCGCGA GGCACTCAGC TTAGCCAGGT

GGAAATCCTG CAGCGTGTCA TAGACTACAT CCTCGACCTT

CAGGTGGTCC TGGCAGAGCC GGCGCCTGGA CCCCCGGACG

GTCCGCATCT CCCGATCCAG ACAGCTGAGC TCACTCCGGA

ACTTGTGATC TCCAAGGACA AGAGGAGCTT TTGCCACTGA
```

The amino acid sequence (SEQ ID NO:4) for mouse Id3 protein is as follows:

```
MKALSPVRGC YEAVCCLSER SLAIARGRGK SPSTEEPLSL

LDDMNHCYSR LRELVPGVPR GTQLSQVEIL QRVIDYILDL

QVVLAEPAPG PPDGPHLPIQ TAELTPELVI SKDKRSFCH
```

In one embodiment of the invention, the rabbit monoclonal antibodies (anti-human Id3 antibodies) only have reactivity toward human Id3 protein and have no substantial reactivity toward mouse Id3 protein; i.e., the antibodies have a ratio of reactivity toward human Id3 protein and mouse Id3 protein of greater than 10:1, preferably 20:1, more preferably 40:1, and most preferably 100:1.

In one embodiment of the invention, the rabbit monoclonal antibodies (anti-mouse Id3 antibodies) only have reactivity toward mouse Id3 protein and have no substantial reactivity toward human Id3 protein; i.e., the antibodies have a ratio of binding constant toward mouse Id3 protein and human Id3 protein of greater than 10:1, preferably 20:1, more preferably 40:1, and most preferably 100:1.

In another embodiment of the invention, the rabbit monoclonal antibodies (anti-mouse/human Id3 antibodies) have substantial reactivity toward both human Id3 and mouse Id3 protein; i.e., the antibodies have a ratio of reactivity toward human Id3 protein and mouse Id3 protein of between 1:2 to 2:1. These antibodies have binding constants, measured with respect to mouse Id3 protein and human Id3 protein, in general greater than $1 \times 10^8$, more preferably $1 \times 10^9$, more preferably $1 \times 10^{10}$, more preferably $1 \times 10^{11}$, more preferably $1 \times 10^{12}$, and most preferably $1 \times 10^{13}$.

The rabbit monoclonal antibodies of this invention are obtained from rabbit hybridomas. These are formed by the fusion of rabbit plasmacytoma cells and B lymphocytes from the spleen cells of rabbits immunized against Id3 conjugates. These rabbit hybridomas that secrete Id3 monoclonal antibodies are produced by the procedure of Knight [Spieker-Polet et al., Proceeding National Academy Science USA; 92: 9348-9352 (1995) and U.S. Pat. No. 5,675,063].

An immunogen of human Id3 is prepared for immunization of rabbits for producing the monoclonal antibody. The immunogen is an immunogenic conjugate of a human Id3 protein and an immunogenic protein formed by any conventional manner. The immunogenic conjugate is preferably prepared as a fusion protein of Id3 with an immunogenic protein having a reactive functional group, particularly a carboxylic acid group, or cloned in frame with the protein of interest. This cloning procedure results in the fusion protein. The immunogenic protein also allows the immunogen to be immobilized either on a purification column or on a solid carrier medium. Any of the commonly used immunogenic proteins such as bovine serum albumin (BSA), keyhole limpet hemocyanin (KLH), egg ovalbumin, bovine thyroglobulin (BTG), yellow fluorescent protein (YFP), or glutathione S-transferase (GST), can be used for this invention. Alternatively, synthetic polyamino acids can be used in place of proteins. Preferred immunogenic proteins are His-tag (His), yellow fluorescent protein (YFP), and glutathione S-transferase (GST). The His, GST or YFP can be cloned at the N-terminal (amino terminal) or the C-terminal (carboxyl terminal) of Id3. The fusion protein can be produced by conventional recombinant techniques for producing fusion proteins. In this method, the plasmid is prepared containing the DNA of human Id3 and the DNA for the immunogenic protein. The plasmid can then be inserted into *E. coli* cells, which then express the fusion protein of Id3-immunogenic protein conjugate. The fusion protein can be purified by utilizing any conventional affinity column and thereafter eluted from the column in a pure form by conventional means. The purified fusion proteins prepared in this manner are used as the immunogen to produce the antibodies.

Rabbits are immununized with the immunogen (human Id3 -immunogenic protein conjugate). Rabbits with high titer against human Id3 protein are selected. B lymphocytes are taken from the selected rabbit and fused with plasmacytoma cell lines developed from transgenic rabbits carrying at least two transgenes, preferably two oncogenes such as myc and abl.

In preparing the rabbit hybridomas, B lymphocytes obtained from the spleen, peripheral blood, lymph nodes or other tissue of the immunized rabbits can be used as the monoclonal antibody producing cells; B lymphocytes obtained from the spleen are preferred. Hybridomas are obtained by fusing such B lymphocytes with an immortal cell line, which is a cell line that imparts long term tissue culture stability on the hybrid cell. In a preferred embodiment of the invention, the immortal cell is a lymphoblastoid cell or a plasmacytoma cell such as a myeloma cell, which is an antibody producing cell and is malignant. Supernatants of the hybridomas are screened to select the optimal hybridomas that have desirable Id3 binding properties. The selected hybridomas are cloned and cryopreserved.

The antibodies produced are tested against various antigens to determine their cross-reactivity, particularly the Id1, Id2, and Id4 of the Id family of proteins. Table 1 shows the reactivity of one type of antibody (rabbit monoclonal anti-human Id3) of the present invention toward various Id proteins. Table 2 shows the reactivity of another type of antibody (anti-mouse Id3) of the present invention toward various proteins. Table 3 shows the reactivity of another type of antibody (rabbit monoclonal anti-mouse/human Id3) of the present invention toward various Id proteins.

TABLE 1

Reactivity of rabbit monoclonal anti-human
Id3 antibodies toward various Id proteins

| Protein | Reactivity (%) |
|---|---|
| Mouse Id3 | <5 |
| Human Id3 | 100 |
| Human Id1, Mouse Id1 | <1 |
| Human Id2, Mouse Id2 | <1 |
| Human Id4, Mouse Id4 | <1 |

TABLE 2

Reactivity of rabbit monoclonal anti-mouse
Id3 antibodies toward various Id proteins

| Protein | Reactivity (%) |
|---|---|
| Mouse Id3 | 100 |
| Human Id3 | <5 |
| Human Id1, Mouse Id1 | <1 |
| Human Id2, Mouse Id2 | <1 |
| Human Id4, Mouse Id4 | <1 |

TABLE 3

Reactivity of rabbit monoclonal anti-mouse/human
Id3 antibodies toward various Id proteins

| Protein | Reactivity (%) |
|---|---|
| Mouse Id3 | 50-200 |
| Human Id3 | 100 |
| Human Id1, Mouse Id1 | <1 |
| Human Id2, Mouse Id2 | <1 |
| Mouse Id4 | <1 |
| Human Id4 | <5 |

Chimeric and humanized monoclonal antibodies can be produced by cloning the antibody expressing genes from the hybridoma cells and employing recombinant DNA methods well known in the art to either join the subsequence of the rabbit IgG variable region to human IgG constant regions or to combine human framework regions with complementary determining regions (CDRs) from a donor rabbit immunoglobulin. An improved method for carrying out humanization of rabbit monoclonal antibodies, which provides antibodies of enhanced affinities is set forth in International Patent Application WO 92/11018.

Polypeptide fragments of the monoclonal antibodies comprising only a portion of the primary antibody structure can be prepared. These polypeptide fragments, which can maintain the activity of the parent monoclonal or even provide improved characteristics, can be produced by proteolytic cleavage of intact antibodies by methods well known in the art, or by inserting stop codons at the desired locations in expression vectors containing the antibody genes using site-directed mutagenesis to produce Fab fragments or (Fab)$_2$ fragments. Single chain antibodies can be produced by joining VL and VH regions with a DNA linker [see Huston et al., Proc. Natl. Acad. Sci. U.S.A., 85:5879-5883 (1988) and Bird et al., Science, 242:423-426 (1988)].

The rabbit-monoclonal antibodies of the present invention are useful for preparing reporter molecule-antibody conjugate. Reporter molecules are any molecules that produce, or can be induced to produce, a detectable signal. Non-limiting examples of reporter molecules include radioactive isotopes, enzymes, enzyme fragments, enzyme substrates, enzyme inhibitors, coenzymes, catalysts, fluorophores, dyes, chemiluminescers, luminescers, or sensitizers; a non-magnetic or magnetic particle, a solid support, a liposome, a ligand, or a receptor. Preferred reporter molecules are enzymes such as horseradish peroxidase, alkaline phosphatase, or β-galactosidase.

Antibodies having reactivity toward human Id3 protein and/or mouse Id3 protein are useful in immunoassays for detecting and/or quantifying Id3 protein of a given species in biological samples, particularly for diagnostic, prognostic, drug monitoring, or research purpose.

Anti-Id3 antibodies are useful to measure Id3 in test systems that combine cells and other materials from both human and murine sources. One example of this type of application is the measurement of Id3 in samples from immuno-compromised mice inoculated with human cancer cells, a common model of human cancer used extensively in efforts to discover agents to treat cancer (Dykes et al., Contrib Oncolo Basel, Karger, 1992, Vol 42, pp 1-22).

Anti-human Id3 antibodies, which are specific for human Id3 and not mouse Id3, are useful in research experiments, for example, in which human tumor cells or bone marrow derived cells are implanted into mice and their fate needs to be followed. Anti-mouse Id3 antibodies, which are specific for mouse Id3 and not human Id3, for example, are useful in the same experiment to confirm the identity of the murine cells around the tumor.

The present invention is directed to a method of determining the concentration of human Id3 or mouse Id3 in a liquid sample. The method comprises the steps of: (a) reacting a liquid sample with an antibody, which binds to human Id3 or mouse Id3 and has no substantial cross-reactivity with human or mouse Id1, Id2, or Id4; (b) forming an immunocomplex between Id3 in the sample and the antibody, and (c) determining the amount of immunocomplex formed. The antibody can be any polyclonal or monoclonal antibody, or its fragment that has high affinity toward human Id3 or mouse Id3, i.e. having a binding constant greater than $1 \times 10^8$, preferably $1 \times 10^9$, more preferably $1 \times 10^{10}$, more preferably $1 \times 10^{11}$, more preferably $1 \times 10^{12}$, and most preferably $1 \times 10^{13}$. The immunoassay is sensitive to detect 0.5 ng/mL of less of Id3 in a sample at 100 μL sample volume.

Immunoassays include sandwich assays and competitive assays (see Sittampalm, et al. (1996) *J. Immunol. Methods*, 190:151-161; Vann, et al.(1990) *Methods Enzymol.* 184:537-541). A sandwich assay is used to determine the concentration of an antigen in a sample. A first antibody is attached to a solid support. When a solution containing an antigen of interest is added to the well, the bound antibody captures the antigen, and any unbound antigen is removed by washing. A second antibody, which recognizes a separate epitope from that of the first antibody, binds to the antigen that is already bound to the solid phase via the primary antibody. Excess secondary antibody is removed by washing. The secondary antibody is often labeled by a reporter molecule to facilitate detection or quantitation.

In a competitive assay, an antigen is bound to a solid support. Unbound antigen is removed by washing and any other protein binding sites on the solid support are tied up by incubation with a blocking reagent (often a nonfat dry milk solution). The solid support is then incubated with known amounts of antigen, sample solution, and antibody-reporter molecule conjugate. The amount of antibody-reporter molecule conjugate that binds to the solid support is inversely proportional to the amount of antigen contained in the sample.

In one embodiment, the present invention is directed to a sandwich assay for determining the concentration of human Id3 or mouse Id3 in a liquid sample. The assay comprises the steps of: (a) reacting a liquid sample with a first antibody attached on a solid support and a second antibody in the liquid phase, wherein the first antibody and the second antibody bind to human Id3 or mouse Id3 at different epitopes and have no substantial cross-reactivity against human or mouse Id1, Id2, or Id4; (b) forming an immunocomplex among Id3 in the sample, the first antibody, and the second antibody; and (c) determining the amount of immunocomplex formed. In one aspect, the Id3 in the liquid sample contacts the first antibody before contacting the second antibody. In another aspect, the liquid sample contacts the first antibody and the second antibody simultaneously. The immunocomplex is preferably determined by detecting the reporter molecule conjugated to the second antibody. The first antibody and the second antibody can be any polyclonal or monoclonal antibody, or its fragment that has high affinity toward human Id3 or mouse Id3 i.e. having a binding constant greater than $1\times10^8$, preferably $1\times10^9$, more preferably $1\times10^{10}$, more preferably $1\times10^{11}$, more preferably $1\times10^{12}$, and most preferably $1\times10^{13}$. Preferably, the second antibody is a rabbit monoclonal antibody and labeled with a reporter molecule.

In another embodiment, the present invention is directed to a competitive assay for determining the concentration of human Id3 or mouse Id3 in a liquid sample. The assay comprises the steps of: (a) contacting the sample with a solid-phase support having surface-attached human Id3 or mouse Id3 molecules in the presence of an antibody labeled with a reporter molecule, wherein said surface-attached Id3 is effective to compete with Id3 in the sample for binding to the antibody, (b) forming an immunocomplex between Id3 in the sample and the antibody, and (c) determining the amount of immunocomplex formed. The antibody can be either a polyclonal antibody, or monoclonal antibody, or its fragment that binds to human Id3 or mouse Id3 with a binding constant greater than $1\times10^8$, preferably $1\times10^9$, more preferably $1\times10^{11}$, more preferably $1\times10^{11}$, more preferably $1\times10^{12}$, and most preferably $1\times10^{13}$; with no substantial cross-reactivity with human Id1, Id2, or Id4. Preferably, the antibody is a rabbit monoclonal antibody and labeled with a reporter molecule.

Any suitable solid support commonly used for immunoassays including, but not limited to polystyrene, nitrocellulose, nylon, latex, can be used for the present invention. Microtiter plates (polystyrene) are an example of the solid support of the present invention.

Antibodies having reactivity toward human Id3 protein or mouse Id3 protein are useful in a method for detecting human Id3 or mouse Id3 in a tissue sample, e.g. western blot and immunohistochemistry staining (IHC staining). The antibody can be either a polyclonal antibody, or monoclonal antibody, or its fragment that binds to human Id3 or mouse Id3 with a binding constant greater than $1\times10^8$, preferably $1\times10^9$, more preferably $1\times10^{10}$, more preferably $1\times10^{11}$, more preferably $1\times10^{12}$, and most preferably $1\times10^{13}$; with no substantial cross-reactivity with human Id1, Id2, or Id4. Preferably, the antibody is a rabbit monoclonal antibody.

The western blot method comprises the steps of (a) obtaining a sample of tissue homogenate or tissue extract; (b) applying the sample on gel; (c) performing gel electrophoresis and separating proteins in the sample by molecular weight; (d) transferring the proteins out of the gel and onto a membrane; (e) reacting the membrane with an antibody that binds to human Id3 or mouse Id3, which forms an immunocomplex with Id3 in the sample; and (f) detecting the immunocomplex.

The IHC staining method comprises the steps of (a) reacting a tissue sample with an antibody that binds to human Id3 or mouse Id3, (b) forming an immunocomplex between Id3 in the tissue sample and the antibody, and (c) detecting the immunocomplex formed by staining.

The immunocomplex in the western blot and IHC staining can be detected by two different approaches, as well known by a skilled person. The antibody can be conjugated to a reporter molecule and the reporter molecule is detected. Alternatively, a secondary antibody (e.g. anti-rabbit IgG or anti-mouse IgG) that is conjugated to a reporter molecule is added to the immunocomplex and binds to the immunocomplex, and the reporter molecule is detected.

The rabbit monoclonal antibody of the present invention can be used for research purpose or for diagnostic purpose. For diagnostic purpose, the method comprises the exposure of a liquid sample or a solid sample known or suspected to contain Id3 to a diagnostic device that includes a diagnostic reagent comprising the rabbit monoclonal antibody under conditions that allow the Id3, if present, to bind to the diagnostic reagent, which can be derivatized for detection before, or after, binding of Id3.

The rabbit monoclonal antibody of the present invention can be used for prognostic test. For prognostic test, the method comprises the exposure of a liquid sample or a solid sample known or suspected to contain Id3 to a prognostic device that includes a prognostic reagent comprising the rabbit monoclonal antibody under conditions that allow the Id3, if present, to bind to the prognostic reagent, which can be derivatized for detection before, or after, binding of Id3.

The rabbit monoclonal antibody of the present invention can be used for drug screening assay. For drug screening assay, the method comprises the exposure of a liquid sample or a solid sample known or suspected to contain Id3 to a drug screening device that includes a drug screening reagent comprising the rabbit monoclonal antibody under conditions that allow the Id3, if present, to bind to the drug screening reagent, which can be derivatized for detection before, or after, binding of Id3.

The following examples further illustrate the present invention. These examples are intended merely to be illustrative of the present invention and are not to be construed as being limiting.

EXAMPLES

Example 1

Preparation of Human Antigen: Transformation of *E. coli* Cells for Production of Cloned Human Id3

E. coli cells were transformed to produce cells capable of providing useful quantities of modified human Id3 proteins suitable for use as antigens. In one embodiment, the full length coding region gene for human Id3 (GenBank Accession No. NM-010495, 68-514 base pairs) was cloned into a pGEX-4T-3 vector (Amersham BioScience, GenBank Accession No. U13855). The pGEX vector allows for cloning the gene of interest, in this case human Id3, in frame with the GST residues (GST-tag). pGEX was treated with the appropriate restriction enzyme (EcoRI) for insertion of human Id3 gene. The resulting hId3-GST vector was used to transform BL21 strain of E. coli (Stratagene). Following Stratagene's transformation protocol, the E. coli competent cells were thawed on ice. After thawing, the cells were gently mixed and 100 µL aliquots of cells were transferred into 14-ml polypropylene round bottom tubes (BD Falcon). 1.7 µL of 1:10 diluted 12.5 M β-mercaptoethanol (β-ME) was added to each tube containing the competent cells to give a final β-ME concentration of 25 mM. The tubes were gently mixed and incubated on ice for 10 minutes with gentle swirling every 2 minutes. 1-50 ng of the hId3-GST vector was added to each transformation reaction and gently mixed. The reaction mixture was incubated on ice for 30 minutes. The transformation reaction mixture was heat-pulsed for 45 seconds in a 42° C. water bath. The incubation reaction was placed on ice for 2 minutes. 0.9 mL of preheated (42° C.) SOC medium was added to each transformation reaction and incubated at 37° C. for 1 hour with shaking at 225-250 rpm. Using a sterile spreader, ~200 mL of the transformed cells were spread onto LB-agar plates containing ampicillin. The plates were incubated overnight at 37° C. Colonies grown overnight were transformed BL21 cells with the pGEX-4T-hId3 plasmid, and the cells transferred and grown in LB media containing appropriate antibiotics (ampicillin) to log phase. The BL21 cells were then aliquoted into 1.5 mL microcentrifuge tube. Glycerol was added to a final concentration of 14% and the cells stored at −80° C. for future use.

Example 2

Preparation of Human Antigen and Immunogen: Production and Purification of Human Id3:GST from Transformed *E. coli*

Human Id3 proteins useful as antigens were produced from cells of Example 1. In one embodiment for protein preparation, the auto-induction system (Novagen) in LB media was inoculated with BL21 with pGEX-4T-hId3 plasmid. The BL21 cells were grown in this system at 30° C. with shaking at 225 rpm. The BL21 cell growth was monitored by checking the optical density of the media at intervals of every 6 hours until the cells were grown to an optical density of 3. The media was then centrifuged at 5000 rpm to pellet the cells. The supernatant was discarded and the pelleted cells were lysed using B-PER lysis reagent (Pierce, Inc.). Following the manufacturer's purification protocol, the Immobilized GST Column was equilibrated with 10 mL of B-PER reagent (Pierce). 10 mL (2×5 mL) of cell lysate was applied to the column and allowed the sample to flow completely through the gel bed. The column was washed with 3 mL of Wash Buffer 1 (Pierce), and can be repeated up to three times. The column was washed with Wash Buffer 2 (Pierce). The elution buffer was prepared using 12 mL of Wash Buffer 2 to one vial containing 184 mg GST. The fusion protein was eluted four times with 3 mL of elution buffer. Each 3 mL fraction was collected and absorbance was measured at 280 nm to monitor the elution of hId3:GST from the column. The protein concentration of hId3:GST was determined. Purity of hId3 was checked using sodium dodecyl sulphate-polyacrylamide gel electrophoresis (SDS-PAGE).

Example 3

Preparation, Production and Purification of Miscellaneous Proteins Used in Antibody Production, Screening and Characterization Various additional Id3-related proteins were produced to use for antibody screening and characterization using the appropriate Id3 DNA in place of the DNA for human Id3. In this manner, the fusion proteins listed in Table 4 were also produced by the procedures of Examples 1 and 2.

TABLE 4

Vectors Used to Make Miscellaneous Proteins Supporting Production Rabbit Antibodies to Mouse Id3 and Human Id3

| Protein | Vector |
| --- | --- |
| Mouse Id1: Histidine | Gene for m-Id1-His litigated into pGW07 |
| Human Id1: Histidine | Gene for h-Id1: his litigated into pGW07 |
| Mouse Id2: Histidine | Gene for m-Id2: His litigated into pGW07 |
| Human Id2: Histidine | Gene for h-Id2: His litigated into pGW07 |
| Mouse Id3: Histidine | Gene for m-Id3: His litigated into pGW07 |
| Human Id3: Histidine | Gene for h-Id3: His litigated into pGW07 |
| Mouse Id4: Histidine | Gene for m-Id4: His litigated into pGW07 |
| Human Id4: Histidine | Gene for h-Id4: His litigated into pGW07 |

Example 4

Procedure for Producing Rabbit Polyclonal Anti-Human Id3

Rabbits were immunized as follows to produce antisera to the Human Id3:GST fusion protein prepared in Example 1 & 2. Each rabbit was initially intradermally injected to ten (10) sites with human Id3:GST prepared in Examples 1 & 2 at 1.0 mg/mL with complete adjuvant. Subsequent boost injections were injected intradermally to ten (10) sites with Id3:GST at 0.3 mg/mL with incomplete adjuvant on days 20, 34, 47, 79, 108, 137 and 159 since initial injection. The immune-response of each rabbit was monitored via ELISA as set forth in Example 5 with human Id3:GST and GST coated micro titer wells. The rabbit antisera were diluted 1:8000 in 0.015M $KPO_4$ buffer, pH 7.4 containing 0.25% (w/v) BSA, 0.85% (w/v) NaCl, and 0.1% (w/v) $NaN_3$ for the ELISA tests. The rabbit with the highest anti-human Id3 antibody titer of the three rabbits was sacrificed on Day 163 after the initial injection. The antiserum obtained from this rabbit prior to sacrifice was purified via DEAE and further purified through a hId3 antigen-affinity column to obtain affinity purified rabbit polyclonal anti-human Id3.

Example 5

Method for Screening Polyclonal Antibody Titer

The method described below was used to determine rabbits that had a polyclonal antibody titer suitable for subsequent monoclonal antibody production.

Materials
1. The microtiter wells used for assays to determine antibody production and reactivity were coated (0.1 µg/well) with the following antigens previously prepared: mouse Id1:His, human Id1:His, mouse Id2-His, human Id2:His, mouse Id3:His, human Id3:His, mouse Id4:His, human Id4:his and GST.
2. Antibody diluent: 0.25% (w/v) BSA in 0.015M $KPO_4$ Buffer, 0.85% (w/v) NaCl, 0.1% (w/v) $NaN_3$, pH=7.40
3. Sera from rabbits immunized with human Id3:GST as described in Example 5 diluted 1:8,000 in antibody diluent.
4. Goat anti-rabbit IgG HRP conjugate diluted 1:15K with conjugate diluent, i.e., 50% (v/v) fetal Bovine Serum in 0.05 M Tris, 1% (v/v) Proclin-300, pH 7.6
5. TMB Reagent
6. Stop Solution (1 N HCl)

Procedure for Preparing Antigen-Coated Plates

The buffers for plate coating were as follows: 0.2 M sodium phosphate ($NaPO_4$) pH 6.5 buffer, 10 mM potassium phosphate ($KPO_4$) pH 7.4 buffer, 1% (w/v) BSA in 10 mM potassium phosphate ($KPO_4$), pH 7.4 buffer with 0.1% (w/v) sodium azide ($NaN_3$), and 2.5% (w/v) sucrose in 10 mM potassium phosphate ($KPO_4$), pH 7.4 buffer.

The plates were coated with the above antigens by the following procedures:
1. Prepare antigen solution by mixing 0.2 M $NaPO_4$ with antigen for the appropriate coating concentration.
2. Stir solution at room temperature for 10 minutes.
3. Saturate pipet delivery system for 10 minutes.
4. Dispense 100 µL of antigen solution into each well.
5. Incubate plates at room temperature overnight (16-24 hours).
6. Shake off the antigen solution.
7. Wash each well with 300 µL of 10 mM $KPO_4$ buffer.
8. Shake off the $KPO_4$ buffer.
9. Dispense 150 µL of 1% BSA solution into each well.
10. Incubate plates at room temperature overnight (16-24 hours).
11. Shake off the BSA solution.
12. Dispense 250 µL of 2.5% sucrose solution into each well.
13. Incubate plates at room temperature for 4 hours.
14. Shake off sucrose solution.
15. Dry in vacuum at room temperature overnight.

Screening Method

The antibodies were screened by the following procedures:
1. Dispense 100 µL of antibody diluent, diluted rabbit polyclonal anti-Id3 (1:1000 to 1:64,000, serial dilution) into appropriate wells.
2. Incubate at room temperature with mechanical shaking at 750 rpm for 90 minutes.
3. Remove the incubation mixture by flicking plate content into an appropriate waste container, followed by rinsing the wells 5 times with distilled water.
4. Strike the wells sharply onto absorbent paper or paper towels to remove all residual water droplets.
5. Dispense 100 µL of Goat Anti-Rabbit IgG-HRP Conjugate Reagent into each well. Gently mix for 5 seconds.
6. Incubate at room temperature with mechanical shaking at 750 rpm for 90 minutes.
7. Repeat procedures 3 and 4.
8. Dispense 100 µL of TMB Reagent into each well. Gently mix for 5 seconds.
9. Incubate at room temperature with mechanical shaking at 750 rpm for 20 minutes.
10. Add 100 µL of Stop Solution (1N HCl) into each well.
11. Gently mix for 10 seconds to ensure a complete mixing.
12. Read optical density (absorbance) at 450 nm.

Results from this assay were used to select the rabbit sera with the highest antibodies titer that selectively reacts with human Id3 or both mouse Id3 and human Id3.

Example 6

Preparation of Rabbit Monoclonal Anti-Human Id3 and Rabbit Monoclonal Anti-Mouse/Human Id3

Transgenic rabbits were created to provide plasmacytoma cells suitable for hybridoma formation with spleenocytes from animals with suitable antibody titer.

(a) Transgenic Rabbits

Single-cell zygotes were injected with a murine $E_\mu$-abl construct at a concentration of 1 µg/ml and implanted into the uterus of pseudo-pregnant females. Offspring were tested at 3-4 weeks of age by Southern blot analysis of peripheral blood lymphocyte DNA for the presence of the $E_\mu$-abl transgene. Rabbits carrying the $E_\mu$-abl transgene were mated with $E_K$-myc transgenic rabbits. The offspring were tested for the presence of both transgenes as described above. In addition, zygotes from a transgenic $E_K$-myc rabbit with the $E_K$-abl transgene were microinjected directly.

(b) Generation of Plasmacytoma Cell Lines and Hypoxanthine/Aminopterin/Thymidine (HAT)-Sensitive Fusion Partner Rabbits that became ill were sacrificed and cells from the tumor tissues were placed in tissue culture in an attempt to obtain plasmacytoma cell lines. Culture medium used was RPMI 1640 enriched with the following additions: amino acids, nonessential amino acids, pyruvate, glutamine, vitamins, Hepes, gentamicin, penicillin, streptomycin, fungizone (all components were from GIBCO and were used at concentrations suggested by the supplier), and 50 µM β-mercaptoethanol. After 6-8 weeks in culture, stable cell lines were growing from these tumor tissues.

To obtain a HAT-sensitive fusion partner, three cell lines were first X-irradiated with 200 rad (1 rad=0.01 Gy) and then cultured in the presence of 8-azaguanine. (The concentration of 8-azaguanine was initially 0.2 µg/ml and was slowly increased to 20 µg/ml over a 10-month period). Three 8-azaguanine-resistant clones were obtained after one month and two after 8 months in culture. Cells of these clones were sensitive to medium containing HAT.

(c) Isolation of Spleenocytes for Rabbit Monoclonal Anti-mouse/Human Id3

Id3-Spleen cells from sacrificed rabbit (Example 4) were harvested and isolated by crushing the spleen in RPMI 1640 medium and filtering through 100-µm strainers, followed by treatment with red cell lysis buffer (Sigma). The isolated spleenocytes were kept in 10% dimethyl sulfoxide and 90% FBS at −80° C. until use.

(d) Hybridoma Development for Rabbit Monoclonal Anti-mouse/Human Id3

To generate the rabbit monoclonal anti-mouse/human Id3 hybridoma, the spleenocytes were fused with the rabbit plasmacytoma cell line in part (b) at a ratio of 2:1 with 50% (w/v) polyethylene glycol (Sigma). Two fusions were performed. The fused cells were plated at a density of $5 \times 10^5$ cells/well in 96-well plates in RPMI 1640 supplemented with 10% fetal bovine serum (FBS), amino acids, vitamins, HEPES, sodium pyruvate, β-mercaptoethanol and antibiotics (gentamicin/penicillin/streptomycin/fungizone). After 24 hour incubation, hypoxanthine, aminopterin, and thymidine (HAT) containing medium was added and FBS was brought up to 15%. Medium in fusion plates was changed after four weeks.

(e) Positive Clone Identification for Rabbit Monoclonal Anti-mouse/Human Id3

Seven days after medium change, positive rabbit monoclonal anti-mouse/human Id3 hybridomas were identified via ELISA, using plates pre-coated with mouse Id3:His and human Id3:His as described in Example 5. Positive hybridoma clones were transferred and expanded into 24-well plates. The expanded hybridoma supernatants were further screened for rabbit monoclonal anti-mouse/human Id3 positive clones by ELISA using plates pre-coated with human Id3:His or GST as described in Example 5. The supernatants from hybridoma clones showing positive on mouse Id3 and/or human Id3:His plates but negative on GST plates were collected for serial dilution ELISA performed to select strong positive clones without cross-reactivity to GST.

Such clones were identified. To ensure for monoclonal hybridoma, the clones were subcloned with limiting dilution. Subclones with high ELISA titers were selected for concentrated antibody production.

(f) Monoclonal Antibody Production

Concentrated antibody production was conducted in an Integra flask. A subclone of the identified clone, was expanded to two T175 flasks in RPMI medium with 10% FBS, 1×HAT and other supplements. Prior to inoculation into an Integra flask, the cells were adapted to a low serum medium (25% RPMI with 10% FBS and 75% BD mAb serum-free medium) overnight. About $2 \times 10^7$ cells were inoculated and grown in BD mAb serum free medium. The medium in nutrient compartment of the flask was changed ten days after inoculation. After another ten days, supernatant in the cell compartment of the flask was harvested.

Example 7

Sequences of Selected Rabbit Monoclonal Antibodies

Both the positive rabbit clones secreting monoclonal antibodies against mouse Id3 and/or human Id3 were selected utilizing the procedures described in Example 5 except rabbit monoclonal anti-human Id3 and rabbit monoclonal anti-mouse/human Id3 from supernatants of the hybridomas produced in Example 6 were used instead of rabbit polyclonal antisera. All supernatants were diluted 1:10 in antibody diluent prior to analysis.

Total RNAs were isolated from hybridomas of Clones #BCH-4/#3-3, #BCH-4/#6-1, #BCH-4/#16-1, #BCH-4/#17-3, and #BCH-4/#42-1, using Qiagen RNaesy Mini Kit (Catalog #74104). cDNAs were made from the total RNA by Oligo dT directed reverse transcription (reverse transcriptase, Promega Improm II, from Promega, Catalog#M314A).

Rabbit IgG cDNA were amplified with heavy or light chain specific primers (designed by Epitomics, Inc., Burlingame, Calif., and synthesized by Elim Biopharmaceuticals, Inc., Hayward, Calif.) by PCR (DNA polymerase, TaqPlus Precision, purchased from Stratagene Corp, La Jolla, Calif., Catalog #600211-51). The IgG heavy and light chain sequences of the selected clone were obtained by sequencing the PCR products (sequencing services provided by Elim Biopharmaceuticals, Inc.). For recombinant expression of anti-Id3 antibody, the PCR product was cloned into pcDNA3 or pTT5 vector. Recombinant Id3 antibody was transiently expressed in HEK 293 cells with plasmid DNA transfection.

The rabbit monoclonal anti-human Id3, clone #BCH-4/#3-3, has the following DNA and amino acid sequence:

```
                     Variable Light Chain Sequence
               (Nucleotide/Peptide, SEQ ID NO. 5/6), 327 nt 1 caagtgctgacccagactccatctcccgtgtctgcagctgtgggaggcacagtcaccatc  60
    Q  V  L  T  Q  T  P  S  P  V  S  A  A  V  G  G  T  V  T  I 61 aattgccaggccagtcagagtatttataatgacaacgacttagcttggtttcagcagaaa 120
    N  C  Q  A  S  Q  S  I  Y  N  D  N  D  L  A  W  F  Q  Q  K 121 ccagggcagcctcccaagctcctgatctatgatgcatccactctgacatctggggtccca 180
    P  G  Q  P  P  K  L  L  I  Y  D  A  S  T  L  T  S  G  V  P 181 Tcgcggttcaaaggcagtggatctgggacacaattcactctcaccatcagcgacctggac 240
    S  R  F  K  G  S  G  S  G  T  Q  F  T  L  T  I  S  D  L  D 241 Tgtgacgatgctgccacttactactgtgcagcccgttatagtggtaatatttatggtttc 300
    C  D  D  A  A  T  Y  Y  C  A  A  R  Y  S  G  N  I  Y  G  F 301 ggcggagggaccgaggtggtggtcaaa
    G  G  G  T  E  V  V  V  K
```

```
                    Variable Heavy Chain Sequence
              (Nucleotide/Peptide, SEQ ID NO. 7/8), 336 nt 1  cagtcggtggaggagtccgggggtcgcctggtcacgcctgggacacccctgacactcacc   60
     Q   S   V   E   E   S   G   G   R   L   V   T   P   G   T   P   L   T   L   T 61  tgcacagtctctggaatcgacctcagtagctatgcaatgagctgggtccgccaggctcca  120
     C   T   V   S   G   I   D   L   S   S   Y   A   M   S   W   V   R   Q   A   P 121  gggaaggggctggaatggatcggagtcattttcctagtaataatgtatattacgcgagc  180
     G   K   G   L   E   W   I   G   V   I   F   P   S   N   N   V   Y   Y   A   S 181  tgggcgaaaggccgattcaccatctccaaaacctcgaccacggtggatctgaaaatcacc  240
     W   A   K   G   R   F   T   I   S   K   T   S   T   T   V   D   L   K   I   T 241  agtccgacaaccgaggacacggccacctatttctgtgccagtatgggtgcttttgattcc  300
     S   P   T   T   E   D   T   A   T   Y   F   C   A   S   M   G   A   F   D   S 301  tggggcccaggcaccctggtcaccgtctcctcaggg
     W   G   P   G   T   L   V   T   V   S   S   G
```

The rabbit monoclonal anti-mouse/human Id3, clone #BCH-4/#6-1, has the following DNA and amino acid sequence:

```
                    Variable Light Chain Sequence
              (Nucleotide/Peptide, SEQ ID NO. 9/10), 333 nt 1  gccgtgctgacccagactccatctcccgtgtctgcagctgtgggaggcacagtcagcatt   60
     A   V   L   T   Q   T   P   S   P   V   S   A   A   V   G   G   T   V   S   I 61  agttgccagtccagtcagagtgtttggaataacaactggttatcctggtttcagcagaaa  120
     S   C   Q   S   S   Q   S   V   W   N   N   N   W   L   S   W   F   Q   Q   K 121  ccagggcagcctcccaagctcctgatctatgaaacatccaaactggaatctggggtccca  180
     P   G   Q   P   P   K   L   L   I   Y   E   T   S   K   L   E   S   G   V   P 181  tcgcggttcaaaggcagtggatctgggacacagttcactctcaccatcagcgacgtgcag  240
     S   R   F   K   G   S   G   S   G   T   Q   F   T   L   T   I   S   D   V   Q 241  tgtgacgatgctgccacttactactgtctaggcggttattggactactagtgataataat  300
     C   D   D   A   A   T   Y   Y   C   L   G   G   Y   W   T   T   S   D   N   N 301  gttttcggcggagggaccgaggtggtggtcaaa
     V   F   G   G   G   T   E   V   V   V   K Variable Heavy Chain Sequence
              (Nucleotide/Peptide, SEQ ID NO. 11/12), 333 nt 1  cagtcggtggaggagtccggcggtcgcctggtcacgcctgggacacccctgacactcacc   60
     Q   S   V   E   E   S   G   G   R   L   V   T   P   G   T   P   L   T   L   T 61  tgcacagcctctggattctccctcagtaatgtctacatacactgggtccgccaggctcca  120
     C   T   A   S   G   F   S   L   S   N   V   Y   I   H   W   V   R   Q   A   P 121  gggaaggggctggaatggatcggatacattagtgatggtgatactgcacgctacgcgacc  180
     G   K   G   L   E   W   I   G   Y   I   S   D   G   D   T   A   R   Y   A   T 181  tgggcgaaaggccgattcaccatctccaaaacctcgtcgaccacggtgaatctgaaaatg  240
     W   A   K   G   R   F   T   I   S   K   T   S   S   T   T   V   N   L   K   M 241  accagtctgacaaccgaggacacggccacctattttgtgccagacagggatttaacatc  300
     T   S   L   T   T   E   D   T   A   T   Y   F   C   A   R   Q   G   F   N   I 301  tggggcccaggcaccctggtcaccgtctcctta
     W   G   P   G   T   L   V   T   V   S   L
```

The rabbit monoclonal anti-mouse/human Id3, clone #BCH-4/#16-1, has the following DNA and amino acid sequence:

```
                    Variable Light Chain Sequence
              (Nucleotide/Peptide, SEQ ID NO. 13/14), 333 nt 1 gccgtgctgacccagactccatctcccgtgtctgcagctgtgggaggcacagtcaccatt  60
    A  V  L  T  Q  T  P  S  P  V  S  A  A  V  G  G  T  V  T  I 61 agttgccagtccagtcagagtgtttataataacaactggttatcctggtttcagcagaaa 120
    S  C  Q  S  S  Q  S  V  Y  N  N  W  L  S  W  F  Q  Q  K 121 tcagggcagcctcccaagctcctgatctatgaaacatccaaactggaatctggggtccca 180
    S  G  Q  P  P  K  L  L  I  Y  E  T  S  K  L  E  S  G  V  P 181 tcgcggttcaaaggcagtggatctgggacacagttcactctcaccatcatcgacgtgcag 240
    S  R  F  K  G  S  G  S  G  T  Q  F  T  L  T  I  I  D  V  Q 241 tgtgacgatgctgccacttactactgtctaggcggttattggactactagtgataataat 300
    C  D  D  A  A  T  Y  Y  C  L  G  G  Y  W  T  T  S  D  N  N 301 attttcggcggagggaccgaggtggtggtcaaa
    I  F  G  G  G  T  E  V  V  V  K Variable Heavy Chain Sequence
              (Nucleotide/Peptide, SEQ ID NO: 15/16), 333 nt 1 cagtcggtggaggagtccggcggtcgcctggtcacgcctgggacacccctgacactcacc  60
    Q  S  V  E  E  S  G  G  R  L  V  T  P  G  T  P  L  T  L  T 61 tgcacagcctctggattctccctcagtagctactacatacactgggtccgccaggctcca 120
    C  T  A  S  G  F  S  L  S  S  Y  Y  I  H  W  V  R  Q  A  P 121 gggaaggcgctggaatggatcggatatattagtgatggtgggactacatactacgcgagc 180
    G  K  A  L  E  W  I  G  Y  I  S  D  G  G  T  T  Y  Y  A  S 181 tgggcgaaaggccgattcaccatctccaaaacctcgtcgaccacggtggatctgaaaatg 240
    W  A  K  G  R  F  T  I  S  K  T  S  S  T  T  V  D  L  K  M 241 accagtctgacaaccgaggacacggccacctatttttgtgccagacagggatttaacatc 300
    T  S  L  T  T  E  D  T  A  T  Y  F  C  A  R  Q  G  F  N  I 301 tggggcccaggcaccctggtcaccgtctcctta
    W  G  P  G  T  L  V  T  V  S  L
```

40

The rabbit monoclonal anti-mouse/human Id3, clone #BCH-4/#17-3, has the following DNA and amino acid sequence:

```
                    Variable Light Chain Sequence
              (Nucleotide/Peptide, SEQ ID NO. 17/18), 333 nt 1 gccgtgctgacccagactccatctcccgtgtctgcagctgtgggaggcacagtcagcatt  60
    A  V  L  T  Q  T  P  S  P  V  S  A  A  V  G  G  T  V  S  I 61 agttgccagtccagtcagagtgtttggaataacaactggttatcctggtttcagcagaaa 120
    S  C  Q  S  S  Q  S  V  W  N  N  W  L  S  W  F  Q  Q  K 121 ccagggcagcctcccaagctcctgatctatgaaacatccaaactggaatctggggtccca 180
    P  G  Q  P  P  K  L  L  I  Y  E  T  S  K  L  E  S  G  V  P 181 tcgcggttcaaaggcagtggatctgggacacagttcactctcaccatcagcgacgtgcag 240
    S  R  F  K  G  S  G  S  G  T  Q  F  T  L  T  I  S  D  V  Q 241 tgtgacgatgctgccacttactactgtctaggcggttattggactactagtgataataat 300
    C  D  D  A  A  T  Y  Y  C  L  G  G  Y  W  T  T  S  D  N  N 301 gttttcggcggagggaccgaggtggtggtcaaa
    V  F  G  G  G  T  E  V  V  V  K
```

| Variable Heavy Chain Sequence (Nucleotide/Peptide, SEQ ID NO. 19/20), 333 nt |
| --- |

```
  1 cagtcggtggaggagtccggcggtcgctggtcacgcctgggacacccctgacactcacc  60
    Q  S  V  E  E  S  G  G  R  L  V  T  P  G  T  P  L  T  L  T 61 tgcacagcctctggattctccctcagtaatgtctacatacactgggtccgccaggctcca 120
    C  T  A  S  G  F  S  L  S  N  V  Y  I  H  W  V  R  Q  A  P 121 gggaaggggctggaatggatcggatacattagtgatggtgatactgcacgctacgcgacc 180
    G  K  G  L  E  W  I  G  Y  I  S  D  G  D  T  A  R  Y  A  T 181 tgggcgaaaggccgattcaccatctccaaaacctcgtcgaccacggtgaatctgaaaatg 240
    W  A  K  G  R  F  T  I  S  K  T  S  S  T  T  V  N  L  K  M 241 accagtctgacaaccgaggacacggccacctattttgtgccagacagggatttaacatc 300
    T  S  L  T  T  E  D  T  A  T  Y  F  C  A  R  Q  G  F  N  I 301 tggggcccaggcaccctggtcaccgtctcctta
    W  G  P  G  T  L  V  T  V  S  L
```

One of the selected rabbit monoclonal anti-mouse/human Id3, clone #BCH-4/#42-1, in Example 7 had the following DNA and amino acid sequence:

| Variable Light Chain Sequence (Nucleotide/Peptide, SEQ ID NO. 21/22), 333 nt |
| --- |

```
  1 gccgtgctgacccagactccatctcccgtgtctgcagctgtggggaggcacagtcaccatc  60
    A  V  L  T  Q  T  P  S  P  V  S  A  A  V  G  G  T  V  T  I 61 agttgccagtccagtcagagtgtttataataacaactggttatcctggtttcagcagaaa 120
    S  C  Q  S  S  Q  S  V  Y  N  N  N  W  L  S  W  F  Q  Q  K 121 tcagggcagcctcccaagctcctgatctacgaaacatccaaactggaatctggggtccca 180
    S  G  Q  P  P  K  L  L  I  Y  E  T  S  K  L  E  S  G  V  P 181 tcgcggttcaaaggcagtggatctgggacacagttcactctcaccatcatcgacgtgcag 240
    S  R  F  K  G  S  G  S  G  T  Q  F  T  L  T  I  I  D  V  Q 241 tgtgacgatgctgccacttactactgtctaggcggttattggagtactagtgataataat 300
    C  D  D  A  A  T  Y  Y  C  L  G  G  Y  W  S  T  S  D  N  N 301 attttcggcggagggaccgaggtggtggtcaaa
    I  F  G  G  G  T  E  V  V  V  K
```

| Variable Heavy Chain Sequence (Nucleotide/Peptide, SEQ ID NO. 23/24), 333 nts |
| --- |

```
  1 cagtcggtggaggagtccggcggtcgcctggtcacgcctgggacacccctgacactcacc  60
    Q  S  V  E  E  S  G  G  R  L  V  T  P  G  T  P  L  T  L  T 61 tgcacagcctctggattctccctcagtagctactacatacactgggtccgccaggctcca 120
    C  T  A  S  G  F  S  L  S  S  Y  Y  I  H  W  V  R  Q  A  P 121 gggaaggcgctggaatggatcggatatattagtgatggtgggactacatactacgcgagc 180
    G  K  A  L  E  W  I  G  Y  I  S  D  G  G  T  T  Y  Y  A  S 181 tgggcgaaaggccgattcaccatctccaaaacctcgtcgaccacggtggatctgaaaatg 240
    W  A  K  G  R  F  T  I  S  K  T  S  S  T  T  V  D  L  K  M 241 accagtctgacaaccgaggacacggccacctattttgtgccagacagggatttaacatc 300
    T  S  L  T  T  E  D  T  A  T  Y  F  C  A  R  Q  G  F  N  I 301 tggggcccaggcaccctggtcaccgtctcctta
    W  G  P  G  T  L  V  T  V  S  L
```

Example 8

Cross-Reactivity of Rabbit Monoclonal Anti-Mouse/Human Id3 and Rabbit Monoclonal Anti-Human Id3 Determined by Western Blot The selected rabbit monoclonal anti-mouse/human Id3 and rabbit monoclonal anti-human Id3 produced in Examples 6 were compared with a commercially available rabbit polyclonal anti-mouse/human Id3 from Santa Cruz Biotechnology Inc., Santa Cruz, Calif., by Western blot analysis. The antibodies were tested at 1:500 and 1:1,000 dilutions by western blotting on Hela (H lane) and 10T1/2 fibroblast whole cell extracts (M lane) at 40 µg per lane. The experiments were performed according to the following procedures:
a. Boil ~40 µg of whole cell extract for ~3 minutes in SDS loading dye. Chill on ice 2 min.
b. Load onto a 15% SDS-polyacrylamid gel and run at 100 V till blue dye is about a cm off the bottom of the gel.
c. Transfer overnight to PVDF membrane at 30 V at 4C (use COLD transfer buffer).
d. The next day, block 1 hour with 5% milk in PBS at room temp (all subsequent steps at RT).
e. Incubate 1 hour with primary antibody diluted in 1% milk+PBS+0.05% TWEEN.
f. Wash 3×5 minutes with PBS+0.05% TWEEN.
g. Incubate 30 minutes with secondary antibody (1:5000 dilution of Amersham's anti-rabbit IgG HRP in 1% milk+PBS+0.05% TWEEN).
h. Wash 3×5 minutes in PBS+0.05% TWEEN.
i. Drain membrane and treat with ECL Plus for 5 minutes
j. Expose to film (initial 5-10 second quick exposures). Depending on intensity, expose for 30 seconds/1 minute/5 minutes/10 minutes/1 hour.

In FIG. 1.1, Santa Cruz Biotechnology's rabbit polyclonal anti-Id3 was used to develop blot A. The rabbit monoclonal anti-mouse/human Id3, clone #BCH-4/#6-1, clone #BCH-4/#16-1, clone #BCH-4/#17-3, and clone #BCH-4/#42-1, of this invention were used to develop blot B, C, D, and E, respectively. The results demonstrate that:
  a. Santa Cruz Biotechnology's rabbit polyclonal anti-Id3 binds to both mouse Id3 and human Id3 from the untransfected cells express either mouse Id3 or human Id3. This antibody also binds to endogenous non-Id3 related materials at other molecular weights.
  b. The rabbit monoclonal anti-mouse/human Id3, clone #BCH-4/#6-1, clone #BCH-4/#16-1, clone #BCH-4/#17-3, and clone #BCH-4/#42-1, of this invention bind to both mouse Id3 and human Id3 from the untransfected cells that express either mouse Id3 or human Id3, but do not bind to endogenous non-Id3 related materials.

In FIG. 1.2, Santa Cruz Biotechnology's rabbit polyclonal anti-Id3 was used to develop blot A. The rabbit monoclonal anti-human Id3, clone #BCH-4/#3-3, of this invention was used to develop blot B. The results demonstrate that:
  a. Santa Cruz Biotechnology's rabbit polyclonal anti-Id3 detects both mouse Id3 and human Id3 in the untransfected cells that express either mouse Id3 or human Id3. This antibody also binds to non-Id3 related materials at other molecular weights.
  b. The rabbit monoclonal anti-human Id3, clone #BCH-4/#3-3, of this invention binds human Id3, but not to mouse Id3 or endogenous non-Id3 related materials from the untransfected cells that express either mouse Id3 or human Id3.

The above results demonstrate that the rabbit monoclonal anti-mouse/human Id3, #BCH-4/#6-1, clone #BCH-4/#16-1, clone #BCH-4/#17-3, and clone #BCH-4/#42-1, of this invention are selective for mouse/human Id3. Rabbit monoclonal anti-human Id3, clone #BCH-4/#3-3, of this invention is selective for human Id3 only. There is no substantial reactivity towards other endogenous proteins in cell extracts by any of the rabbit monoclonal antibodies. Conversely, the rabbit polyclonal anti-Id3 from Santa Cruz Biotechnology is not specific to Id3 as it also reacts with other endogenous proteins, which makes this antibody unsuitable for unequivocal Id3 detection in tissue samples.

Example 9

Cross Reactivity of Rabbit Monoclonal Anti-Human Id3, and Rabbit Monoclonal Anti-Mouse/Human Id3 Determined by ELISA The rabbit monoclonal anti-human Id3 (clone #3-3) and the rabbit monoclonal anti-mouse/human Id3 (clones #6-1, 16-1, 17-3, and 42-1) produced in Example 6 were tested reactivity against the following antigens: mouse Id1:His, human Id1:His, mouse Id2:His, human Id2:His, mouse Id3:His, human Id3:His, mouse Id4:His, human Id4:His and GST.

Materials
1. Microtiter wells (prepared in accordance with Example 6) were coated (0.1 µg/well) with mouse Id1:His, human Id1:His, mouse Id2:His, human Id3:His, and 1.0 µg/well with GST.
2. Antibody Diluent: 0.25% (w/v) BSA in 0.015M $KPO_4$ Buffer, 0.85% (w/v) NaCl, 0.1% (w/v) $NaN_3$, pH=7.40
3. Rabbit monoclonal anti-human Id3 (clone #3-3) prepared in Example 7 was diluted to 0.005, 0.010, 0.025, 0.05, 0.10, 0.25, and 0.50 µ/ml with the antibody diluent.
4. Rabbit monoclonal anti-mouse/human Id3 (clones #6-1, 16-1, 17-3, 42-1) prepared in Example 7 was diluted to 0.005, 0.010, 0.025, 0.05, 0.10, 0.25, and 0.50 µg/ml with the antibody diluent.
5. Conjugate Diluent: 50% (v/v) which consists of an aqueous solution containing Fetal Bovine Serum in 0.05 M Tris, 1% (v/v) Proclin-300, pH 7.6.
6. Conjugate: Goat anti-rabbit IgG (H+L)-HRP conjugate.
7. TMB reagent.
8. Stop solution (1 N HCl).

Method
Subclones were assayed against the above antigen coated on the microtiter plate walls by the following procedure:
1. Dispense 100 µL of antibody diluent, diluted rabbit monoclonal human Id3, and mouse/human Id3 hybridoma supernatants into appropriate wells.
2. Incubate at room temperature with mechanical shaking at 750 rpm for 90 minutes.
3. Remove the incubation mixture by flicking plate content into an appropriate waste container followed by rinsing the wells 5 times with distilled water.
4. Strike the wells sharply onto absorbent paper or paper towels to remove all residual water droplets.
5. Dispense 100 µL of 1:50,000 Goat Anti-Rabbit IgG-HRP Conjugate Reagent into each well. Gently mix for 5 seconds.
6. Incubate at room temperature with mechanical shaking at 750 rpm for 90 minutes.
7. Repeat procedures 3 and 4.
8. Dispense 100 µL of TMB Reagent into each well. Gently mix for 5 seconds.
9. Incubate at room temperature with mechanical shaking at 750 rpm for 20 minutes.

10. Add 100 μL of Stop Solution (1N HCl) into each well.
11. Gently mix for 10 seconds to ensure a complete mixing.
12. Read optical density at A450 nm.

Tables 5.1 to 5.9 show the results of rabbit monoclonal antibodies, anti-mouse/human Id3 (#6-1, #16-1, #17-3, and #42-1), and anti-human Id3 (#3-3) on binding to (a) Mouse Id1: His Antigen-coated wells, (b) Human Id1: His Antigen-coated wells, (c) Mouse Id2: His Antigen-coated wells, (d) Human Id2: His Antigen-coated wells, (e) Mouse Id3: His Antigen-coated wells, (f) Human Id3: His Antigen-coated wells, (g) Mouse Id4: His Antigen-coated wells, (h) Human Id4: His Antigen-coated wells, and (i) GST Antigen-coated wells.

TABLE 5-1

Mouse Id1: His-coated wells

| Ab Conc. (μg/ml) | h Id3 MoAb 3-3 $A_{450}$ | m/h Id3 MoAb 6-1 $A_{450}$ | m/h Id3 MoAb 16-1 $A_{450}$ | m/h Id3 MoAb 17-3 $A_{450}$ | m/h Id3 MoAb 42-1 $A_{450}$ |
|---|---|---|---|---|---|
| 0.000 | 0.047 | 0.045 | 0.044 | 0.045 | 0.052 |
| 0.005 | 0.044 | 0.047 | 0.046 | 0.048 | 0.045 |
| 0.010 | 0.047 | 0.044 | 0.050 | 0.047 | 0.043 |
| 0.025 | 0.044 | 0.046 | 0.044 | 0.045 | 0.045 |
| 0.050 | 0.049 | 0.046 | 0.044 | 0.048 | 0.050 |
| 0.100 | 0.047 | 0.049 | 0.047 | 0.051 | 0.049 |
| 0.250 | 0.048 | 0.048 | 0.047 | 0.052 | 0.054 |
| 0.500 | 0.050 | 0.051 | 0.047 | 0.060 | 0.053 |

TABLE 5-2

Human Id1: His-coated wells

| Ab Conc. (μg/ml) | h Id3 MoAb 3-3 $A_{450}$ | m/h Id3 MoAb 6-1 $A_{450}$ | m/h Id3 MoAb 16-1 $A_{450}$ | m/h Id3 MoAb 17-3 $A_{450}$ | m/h Id3 MoAb 42-1 $A_{450}$ |
|---|---|---|---|---|---|
| 0.000 | 0.046 | 0.045 | 0.043 | 0.045 | 0.043 |
| 0.005 | 0.047 | 0.044 | 0.042 | 0.044 | 0.046 |
| 0.010 | 0.046 | 0.049 | 0.042 | 0.046 | 0.045 |
| 0.025 | 0.049 | 0.048 | 0.046 | 0.047 | 0.043 |
| 0.050 | 0.050 | 0.052 | 0.047 | 0.044 | 0.045 |
| 0.100 | 0.047 | 0.049 | 0.047 | 0.048 | 0.047 |
| 0.250 | 0.047 | 0.051 | 0.045 | 0.045 | 0.044 |
| 0.500 | 0.048 | 0.048 | 0.051 | 0.049 | 0.047 |

TABLE 5-3

Mouse Id2: His-coated wells

| Ab Conc. (μg/ml) | h Id3 MoAb 3-3 $A_{450}$ | m/h Id3 MoAb 6-1 $A_{450}$ | m/h Id3 MoAb 16-1 $A_{450}$ | m/h Id3 MoAb 17-3 $A_{450}$ | m/h Id3 MoAb 42-1 $A_{450}$ |
|---|---|---|---|---|---|
| 0.000 | 0.048 | 0.044 | 0.046 | 0.048 | 0.048 |
| 0.005 | 0.048 | 0.046 | 0.045 | 0.052 | 0.050 |
| 0.010 | 0.045 | 0.048 | 0.049 | 0.048 | 0.050 |
| 0.025 | 0.048 | 0.048 | 0.051 | 0.050 | 0.052 |
| 0.050 | 0.048 | 0.051 | 0.051 | 0.054 | 0.051 |
| 0.100 | 0.050 | 0.055 | 0.055 | 0.057 | 0.058 |
| 0.250 | 0.051 | 0.062 | 0.063 | 0.064 | 0.063 |
| 0.500 | 0.050 | 0.066 | 0.067 | 0.069 | 0.075 |

TABLE 5-4

Human Id2: His-coated wells

| Ab Conc. (μg/ml) | h Id3 MoAb 3-3 $A_{450}$ | m/h Id3 MoAb 6-1 $A_{450}$ | m/h Id3 MoAb 16-1 $A_{450}$ | m/h Id3 MoAb 17-3 $A_{450}$ | m/h Id3 MoAb 42-1 $A_{450}$ |
|---|---|---|---|---|---|
| 0.000 | 0.043 | 0.045 | 0.049 | 0.043 | 0.044 |
| 0.005 | 0.044 | 0.045 | 0.046 | 0.045 | 0.043 |
| 0.010 | 0.043 | 0.044 | 0.044 | 0.043 | 0.046 |
| 0.025 | 0.044 | 0.045 | 0.045 | 0.054 | 0.071 |
| 0.050 | 0.048 | 0.046 | 0.044 | 0.049 | 0.047 |
| 0.100 | 0.048 | 0.049 | 0.048 | 0.048 | 0.046 |
| 0.250 | 0.054 | 0.056 | 0.052 | 0.054 | 0.051 |
| 0.500 | 0.047 | 0.063 | 0.058 | 0.053 | 0.057 |

TABLE 5-5

Mouse Id3: His-coated wells

| Ab Conc. (μg/ml) | h Id3 MoAb 3-3 $A_{450}$ | m/h Id3 MoAb 6-1 $A_{450}$ | m/h Id3 MoAb 16-1 $A_{450}$ | m/h Id3 MoAb 17-3 $A_{450}$ | m/h Id3 MoAb 42-1 $A_{450}$ |
|---|---|---|---|---|---|
| 0.000 | 0.053 | 0.047 | 0.044 | 0.047 | 0.047 |
| 0.005 | 0.045 | 0.312 | 0.240 | 0.390 | 0.437 |
| 0.010 | 0.046 | 0.539 | 0.432 | 0.690 | 0.756 |
| 0.025 | 0.053 | 1.126 | 0.953 | 1.402 | 1.582 |
| 0.050 | 0.050 | 1.753 | 1.575 | 2.195 | 2.235 |
| 0.100 | 0.046 | 2.557 | 2.277 | 2.906 | 2.872 |
| 0.250 | 0.047 | 3.421 | 3.212 | 3.615 | 3.549 |
| 0.500 | 0.047 | 3.811 | 3.610 | 3.742 | 3.628 |

TABLE 5-6

Human Id3: His-coated wells

| Ab Conc. (μg/ml) | h Id3 MoAb 3-3 $A_{450}$ | m/h Id3 MoAb 6-1 $A_{450}$ | m/h Id3 MoAb 16-1 $A_{450}$ | m/h Id3 MoAb 17-3 $A_{450}$ | m/h Id3 MoAb 42-1 $A_{450}$ |
|---|---|---|---|---|---|
| 0.000 | 0.044 | 0.043 | 0.046 | 0.045 | 0.044 |
| 0.005 | 0.285 | 0.275 | 0.228 | 0.330 | 0.382 |
| 0.010 | 0.484 | 0.491 | 0.391 | 0.581 | 0.713 |
| 0.025 | 1.061 | 0.974 | 0.802 | 1.273 | 1.438 |
| 0.050 | 1.627 | 1.610 | 1.399 | 1.796 | 1.995 |
| 0.100 | 2.371 | 2.362 | 1.989 | 2.603 | 2.604 |
| 0.250 | 2.984 | 3.019 | 2.828 | 3.318 | 3.315 |
| 0.500 | 3.382 | 3.556 | 3.371 | 3.688 | 3.749 |

TABLE 5-7

Mouse Id4: His-coated wells

| Ab Conc. (μg/ml) | h Id3 MoAb 3-3 $A_{450}$ | m/h Id3 MoAb 6-1 $A_{450}$ | m/h Id3 MoAb 16-1 $A_{450}$ | m/h Id3 MoAb 17-3 $A_{450}$ | m/h Id3 MoAb 42-1 $A_{450}$ |
|---|---|---|---|---|---|
| 0.000 | 0.046 | 0.046 | 0.046 | 0.048 | 0.051 |
| 0.005 | 0.046 | 0.048 | 0.045 | 0.045 | 0.050 |
| 0.010 | 0.045 | 0.046 | 0.046 | 0.050 | 0.051 |
| 0.025 | 0.047 | 0.044 | 0.045 | 0.047 | 0.048 |
| 0.050 | 0.050 | 0.046 | 0.046 | 0.050 | 0.048 |
| 0.100 | 0.049 | 0.048 | 0.046 | 0.049 | 0.054 |
| 0.250 | 0.048 | 0.050 | 0.051 | 0.053 | 0.063 |
| 0.500 | 0.052 | 0.055 | 0.053 | 0.059 | 0.062 |

TABLE 5-8

Human Id4: His-coated wells

| Ab Conc. (µg/ml) | h Id3 MoAb 3-3 $A_{450}$ | m/h Id3 MoAb 6-1 $A_{450}$ | m/h Id3 MoAb 16-1 $A_{450}$ | m/h Id3 MoAb 17-3 $A_{450}$ | m/h Id3 MoAb 42-1 $A_{450}$ |
|---|---|---|---|---|---|
| 0.000 | 0.047 | 0.049 | 0.052 | 0.045 | 0.046 |
| 0.005 | 0.049 | 0.059 | 0.065 | 0.071 | 0.076 |
| 0.010 | 0.046 | 0.074 | 0.070 | 0.065 | 0.085 |
| 0.025 | 0.048 | 0.132 | 0.100 | 0.127 | 0.125 |
| 0.050 | 0.052 | 0.199 | 0.160 | 0.203 | 0.164 |
| 0.100 | 0.058 | 0.239 | 0.193 | 0.237 | 0.207 |
| 0.250 | 0.066 | 0.371 | 0.293 | 0.296 | 0.259 |
| 0.500 | 0.075 | 0.411 | 0.352 | 0.314 | 0.293 |

TABLE 5-9

GST-coated wells

| Ab Conc. (µg/ml) | h Id3 MoAb 3-3 $A_{450}$ | m/h Id3 MoAb 6-1 $A_{450}$ | m/h Id3 MoAb 16-1 $A_{450}$ | m/h Id3 MoAb 17-3 $A_{450}$ | m/h Id3 MoAb 42-1 $A_{450}$ |
|---|---|---|---|---|---|
| 0.000 | 0.044 | 0.047 | 0.048 | 0.046 | 0.048 |
| 0.005 | 0.045 | 0.046 | 0.048 | 0.048 | 0.048 |
| 0.010 | 0.045 | 0.046 | 0.046 | 0.046 | 0.045 |
| 0.025 | 0.048 | 0.049 | 0.048 | 0.045 | 0.045 |
| 0.050 | 0.048 | 0.047 | 0.046 | 0.046 | 0.049 |
| 0.100 | 0.048 | 0.047 | 0.049 | 0.052 | 0.049 |
| 0.250 | 0.048 | 0.051 | 0.048 | 0.052 | 0.051 |
| 0.500 | 0.050 | 0.054 | 0.053 | 0.053 | 0.049 |

Conclusions

1. Rabbit monoclonal anti-mouse/human Id3 (#6-1, #16-1, #17-3, and #42-1) had very high ELISA bindings against mouse Id3 and human Id3 but less than 1% cross reactivity with mouse Id1, human Id1, mouse Id2, human Id2, or mouse Id4. However, these four MoAbs have very minor cross reactivity (<5%) with human Id4.
2. Rabbit monoclonal anti-human Id3 (#3-3) had high ELISA binding against human Id3 but less than 1% cross reactivity with mouse Id1, human Id1, mouse Id2, human Id2, mouse Id3, mouse Id4 or human Id4.
3. All the rabbit monoclonal anti-mouse/human Id3 (#6-1, #16-1, #17-3, and #42-1) and rabbit monoclonal anti-human Id3 (clone #3-3) showed less than 1% cross reactivity with the carrier protein GST.

Tables 6-1 to 6-2 summarize the cross-reactivity of (1) rabbit monoclonal anti-human Id3 (#3-3), and (2) rabbit monoclonal anti-mouse Id3/anti-human Id3 (#6-1, #16-1, #17-3, #42-1) toward Id proteins.

TABLE 6-1

Cross-reactivity of rabbit monoclonal anti-human Id3 (#3-3) toward Id proteins

| Protein | Cross-reactivity (%) |
|---|---|
| Mouse Id1, Human Id1 | <1 |
| Mouse Id2, Human Id2 | <1 |
| Mouse Id3 | <1 |
| Human Id3 | 100 |
| Mouse Id4, Human Id4 | <1 |

TABLE 6-2

Cross-reactivity of rabbit monoclonal anti-mouse/human Id3 (#6-1, #16-1, #17-3, and #42-1) toward Id proteins

| Protein | Cross-reactivity (%) |
|---|---|
| Mouse Id1, Human Id1 | <1 |
| Mouse Id2, Human Id2 | <1 |
| Mouse Id3 | 100 |
| Human Id3 | 100 |
| Mouse Id4 | <1 |
| Human Id4 | <5 |

Example 10

Cross-Reactivity of Rabbit Monoclonal Anti-Mouse Id3 Determined by ELISA

The rabbit monoclonal anti-mouse Id3 (clone #228) was tested for reactivity against the following antigens: mouse Id1:His, human Id1:His, mouse Id2:His, human Id2:His, mouse Id3:His, human Id3:His, mouse Id4:His, and human Id4:His. The materials and method are the same as those described in Example 9 except the following.

Rabbit monoclonal anti-mouse Id3, hybridoma supernatant was used as the test antibody. Protein G purified, rabbit monoclonal anti-mouse/human Id3 antibody, BCH-4/6-1, 0.92 mg/ml in 0.25% BSA was used as positive controls. The results are shown in Table 7.

TABLE 7

Cross-reactivity of rabbit monoclonal anti-mouse Id3 toward Id proteins.

| Coated Wells | Human Id1 $A_{450}$ | Mouse Id1 $A_{450}$ | Human Id2 $A_{450}$ | Mouse Id2 $A_{450}$ | Human Id3 $A_{450}$ | Mouse Id3 $A_{450}$ | Human Id4 $A_{450}$ | Mouse Id4 $A_{450}$ |
|---|---|---|---|---|---|---|---|---|
| Ab Dil 1:5 | 0.047 | 0.049 | 0.047 | 0.045 | 0.051 | 2.398 | 0.046 | 0.049 |
| Ab Dil 1:10 | 0.047 | 0.047 | 0.047 | 0.045 | 0.048 | 1.944 | 0.046 | 0.046 |
| Positive Control 0.50 µg/ml | 2.131 | 2.196 | 3.232 | 3.097 | 2.828 | 3.176 | 0.176 | 0.272 |
| Positive Control 0.25 µg/ml | 2.117 | 1.955 | 2.536 | 2.437 | 2.687 | 2.812 | 0.117 | 0.170 |

Conclusion:

Rabbit monoclonal anti-mouse Id3 (#228) had high ELISA binding against mouse Id3 but <1% cross reactivity with mouse Id1, human Id1, mouse Id2, human Id2, human Id3, mouse Id4 or human Id4.

Example 11

Cross-Reactivity of Rabbit Monoclonal Anti-Mouse/Human Id3 and Commercial Rabbit Polyclonal Antibody Determined by ELISA Cross-reactivity of rabbit monoclonal anti-mouse/human Id3 (clone #6-1) and commercial rabbit polyclonal antibody (Santa Cruz Biotechnology) were determined according to the procedures of Example 9. Table 6 shows the results of rabbit monoclonal antibody (clone #6-1) and commercial rabbit polyclonal antibody on binding to (a) Mouse Id1:His, Mouse Id2:His, Mouse Id3:His, and Mouse Id4:His-coated wells, and (b) Human Id1:His, Human Id2:His, Human Id3:His, and Human Id4:His-coated wells.

TABLE 8

| | Santa Cruz rabbit polyclonal anti-m/h Id3 | | | | | Rabbit monoclonal anti-m/h Id3 (# 6-1) | | | |
|---|---|---|---|---|---|---|---|---|---|
| Ab Conc. (µg/ml) | Mouse Id1: His well A450 | Mouse Id2: His well A450 | Mouse Id3: His well A450 | Mouse Id4: His well A450 | Ab Conc. (µg/ml) | Mouse Id1: His well A450 | Mouse Id2: His well A450 | Mouse Id3: His well A450 | Mouse Id4: His well A450 |
| (a). Mouse Id1: His, Mouse Id2: His, Mouse Id3: His, and Mouse Id4: His-coated wells | | | | | | | | | |
| 0 | 0.057 | 0.060 | 0.055 | 0.048 | 0 | 0.061 | 0.058 | 0.048 | 0.045 |
| 0.005 | 0.069 | 0.071 | 0.058 | 0.041 | 0.005 | 0.076 | 0.073 | 0.295 | 0.039 |
| 0.010 | 0.075 | 0.073 | 0.077 | 0.040 | 0.010 | 0.079 | 0.071 | 0.530 | 0.040 |
| 0.025 | 0.074 | 0.079 | 0.150 | 0.041 | 0.025 | 0.072 | 0.076 | 1.148 | 0.040 |
| 0.050 | 0.089 | 0.095 | 0.224 | 0.045 | 0.050 | 0.093 | 0.093 | 1.723 | 0.042 |
| 0.100 | 0.089 | 0.075 | 0.422 | 0.040 | 0.100 | 0.085 | 0.067 | 2.421 | 0.042 |
| 0.250 | 0.060 | 0.126 | 0.869 | 0.043 | 0.250 | 0.058 | 0.071 | 3.128 | 0.045 |
| 0.500 | 0.069 | 0.170 | 1.318 | 0.047 | 0.500 | 0.067 | 0.073 | 3.466 | 0.043 |
| (b). Human Id1: His, Human Id2: His, Human Id3: His and Human Id4: His- coated wells | | | | | | | | | |
| 0 | 0.060 | 0.058 | 0.054 | 0.045 | 0 | 0.058 | 0.064 | 0.047 | 0.047 |
| 0.005 | 0.074 | 0.074 | 0.076 | 0.045 | 0.005 | 0.075 | 0.076 | 0.248 | 0.060 |
| 0.010 | 0.079 | 0.071 | 0.119 | 0.041 | 0.010 | 0.078 | 0.071 | 0.480 | 0.066 |
| 0.025 | 0.071 | 0.085 | 0.263 | 0.042 | 0.025 | 0.073 | 0.088 | 1.013 | 0.098 |
| 0.050 | 0.091 | 0.090 | 0.464 | 0.043 | 0.050 | 0.091 | 0.086 | 1.518 | 0.140 |
| 0.100 | 0.082 | 0.067 | 0.831 | 0.050 | 0.100 | 0.083 | 0.058 | 1.982 | 0.218 |
| 0.250 | 0.055 | 0.074 | 1.424 | 0.060 | 0.250 | 0.061 | 0.071 | 2.742 | 0.313 |
| 0.500 | 0.060 | 0.090 | 1.873 | 0.061 | 0.500 | 0.062 | 0.062 | 3.296 | 0.357 |

Conclusions
1. Commercial (Santa Cruz) rabbit polyclonal anti-Id3 had much lower titers against mouse Id3 and human Id3 compared with rabbit monoclonal anti-mouse/human Id3.
2. Commercial (Santa Cruz) rabbit polyclonal anti-Id3 showed <1% cross reactivity with mouse Id1, human Id1, human Id2, mouse Id4, or human Id4 but had some cross reactivity (<5%) with mouse Id2, whereas rabbit monoclonal anti-mouse/human Id3 showed no cross reactivity with mouse Id1, human Id1, mouse Id2, human Id2, or mouse Id4 but had some (<5%) cross reactivity with human Id4.

Example 12

Comparison Analysis by Immunohistochemistry (IHC) of Mouse Embryonic Brain Sections by Normal Rabbit IgG and Rabbit Monoclonal Anti-Mouse/Human Id3

For this experiment, the tissue was fixed overnight in 4% paraformaldehyde and washed in 1×PBS+calcium and magnesium. Then 10 µm transversal frozen sections of embryonic day 13.5 mouse heads were cut. The pictures were taken from the third ventricle neuroepithelium and adjacent blood vessels in the brain. Id3 Staining is observed by 3,3'-Diaminobenzidine (DAB) staining. Blood vessels are identified by fluorescein isothiocyanate (FITC)-conjugated isolectin B4. Nuclei are identified by 4'-6-Diamidino-2-phenylindole (DAPI) staining. The isotype-matched IgG control was totally negative, which rules out the possibility of secondary antibody-related background staining.

Procedure:
1. Slides with frozen sections were air dried and blocked for 1 hour in blocking buffer (3% donkey serum, 0.1% triton X-100, PBS).
2. Primary antibodies (rabbit monoclonal anti-mouse/human Id3 or normal rabbit IgG) were diluted in blocking buffer and spread on top of sections. Sections were covered with a square piece of parafilm to ensure even distribution.
3. Sections were washed 3 times in PBS for 5 minutes each time.
4. Sections were incubated with anti-rabbit IgG-biotin conjugated secondary antibody for 1 hour at room temperature.
5. Sections were washed 3 times in PBS for 5 minutes each time.
6. Sections were treated with 0.03% $H_2O_2$ for 10 minutes at room temperature.
7. Avidin/Biotin Complex regent was prepared at least 30 minutes before application.
8. Slides were incubated with ABC reagent for 30 minutes at room temperature.
9. Slides were washed 3 times in PBS for 5 minutes each time.
10. Samples were developed with DAB separately timed for 5 minutes each and rinsed at least 3 times in tap water.
11. Slides were incubated for 1 hour at room temperature with a mixture of Isolectin $B_4$ (1:50) and DAPI (1:100) diluted in blocking buffer.

12. Slides were washed 3 times in PBS for 5 minutes at room temperature.
13. Slides were mounted using hard set vectashield mounting media and after 10 minutes sealed with nail polish.

FIGS. 2A-2E show the fluorescence microscopy immunohistochemistry staining results by using the rabbit monoclonal anti-Id3 of this invention to detect mouse Id3 in embryonic mouse brain sections (E13.5).

FIG. 2A shows the results of a negative control of purified rabbit IgG (5 μg/ml). No Id3 staining was observed with normal rabbit IgG. Red blood cells were observed in the red channel as characteristic concave cells within the vessel profile.

FIG. 2B shows the results of rabbit monoclonal anti-mouse/human Id3, Clone #BCH-4/#6-1. Specific Id3 nuclear localization to neuralepithelium of the third ventricle was observed.

FIG. 2C shows the results of rabbit monoclonal anti-mouse/human Id3, Clone #BCH-4/#16-1. Specific Id3 nuclear localization to neuralepithelium of the third ventricle was observed.

FIG. 2D shows the results of rabbit monoclonal anti-mouse/human Id3, Clone #BCH-4/#17-3. It had Id3 nuclear localization but also with additional cytoplasmic labeling.

FIG. 2E shows the results of rabbit monoclonal anti-mouse/human Id3, Clone #BCH-4/#42-1. Specific Id3 nuclear localization to neuralepithelium of the third ventricle was observed.

Example 13

ELISA Sandwich Assay (a) Rabbit monoclonal anti-mouse/human Id3 (#6-1) and (b) rabbit monoclonal anti-mouse/human Id3 (#16-1) were coated on microtiter plates and used as capture antibodies in ELISA sandwich assays.

Materials
1. Microtiter wells: Coated with (a) rabbit monoclonal anti-mouse/human Id3 (#6-1), or (b) rabbit monoclonal anti-mouse/human Id3 (#16-1)
2. Conjugate: Rabbit polyclonal anti-mouse/human Id3 (Rabbit #C-3210)-HRP. This polyclonal antibody was affinity purified by an Id3 antigen affinity column.
3. Conjugate: Rabbit polyclonal anti-mouse/human Id3 (Rabbit #C-3211)-HRP. This polyclonal antibody was affinity purified by an Id3 antigen affinity column.
4. Standards: Mouse Id3:His prepared in fetal bovine serum
5. Standards: Human Id3:His prepared in fetal bovine serum
6. Conjugate Diluent: 50% (v/v) fetal bovine serum in 0.05 M Tris, 1% (v/v) Proclin-300, pH 7.6
7. TMB Reagent
8. 1 N HCl as Stop Solution Procedure
A. Preparation of Working Conjugate:
1. Rabbit polyclonal anti-mouse/human Id3 (Rabbit C-3210)-HRP was diluted 1:4,000 for (a), and 1:8,000 for (b).
2. Rabbit polyclonal anti-mouse/human Id3 (Rabbit #C-3211)-HRP was diluted 1:250 for (c).
B. Standard Preparation:
50 ng/ml, 25 ng/ml, 10 ng/ml, 5 ng/ml, 2.5 ng/ml and 1 ng/ml of mouse Id3:His antigen or human Id3:His antigen are prepared in fetal bovine serum.

Assay
1. Secure the desired number of separate rabbit monoclonal anti-mouse/human Id3 coated wells in the holder.
2. Separately pipette 100 μL of mouse Id3 or human Id3 standards into appropriate wells.
3. Thoroughly mix for 30 seconds.
4. Incubate at room temperature (18~25° C.) for 90 minutes with mechanical shaking at 750 rpm.
5. Remove the incubation mixture by emptying the plate contents into a waste container.
6. Rinse and empty the microtiter plate 5 times with distilled water. Strike the microtiter plate sharply onto absorbent paper or paper towels to remove all residual water droplets.
7. Dispense either 100 μL of rabbit polyclonal anti-mouse/human Id3-HRP (from Rabbit #C-3210 or Rabbit #C-3211) conjugate into each well.
8. Thoroughly mix for 30 seconds.
9. Incubate at room temperature (18~25° C.) for 90 minutes with mechanical shaking at 750 rpm.
10. Repeat Step 5 and 6.
11. Dispense 100 μL of TMB into each well.
12. Mix gently for 5 seconds.
13. Incubate at room temperature (18~25° C.) for 20 minutes with mechanical shaking at 750 rpm.
14. Dispense 100 μL of 1 N HCl into each well.
15. Mix well for 30 seconds.
16. Read absorbance at 450 nm with a microtiter well reader within 15 minutes.

Figure 3A:
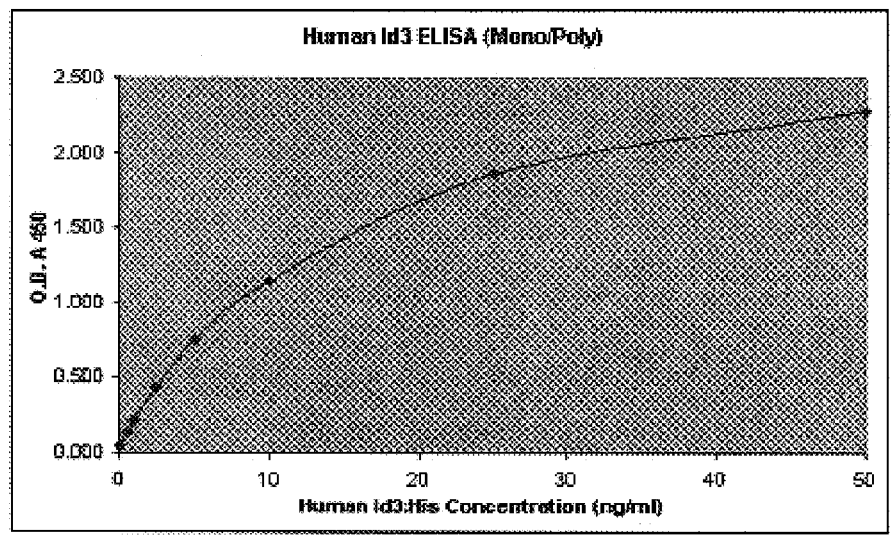
FIGS. 3A and 3B show human Id3 ELISA standard curves obtained using rabbit monoclonal anti-m/h Id3, clone #6-1 (FIG. 3A) or clone #16-1 (FIG. 3B) as a capture antibody in a standard ELISA format.
Figure 3B:
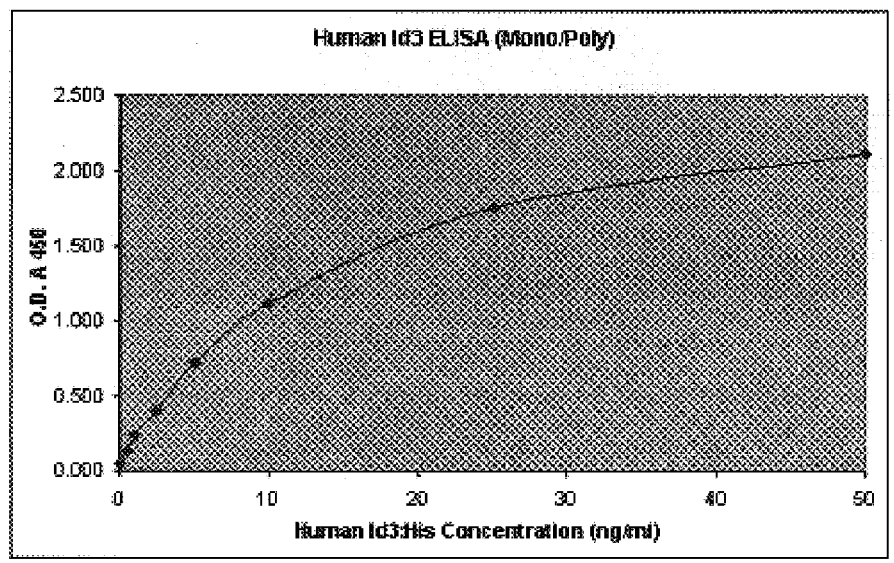

The results of the ELISA readings are shown in FIGS. 3A-3B.

FIG. 3A is a mono/poly ELISA System. Rabbit monoclonal anti-mouse/human Id3, clone #BCH-4/#6-1, was used as a capture antibody and rabbit polyclonal anti-mouse/human Id3 (Rabbit #C-3210, affinity purified) was used as a detection antibody.

FIG. 3B is a mono/poly ELISA System. Rabbit monoclonal anti-mouse/human Id3, clone #BCH-4/#16-1, was used as a capture antibody and rabbit polyclonal anti-mouse/human Id3 (Rabbit #C-3210, affinity purified) was used as a detection antibody.

These examples demonstrate that the ELISA calibration curves obtained using rabbit monoclonal anti-mouse/human Id3 (Clone #BCH-4/#6-1 and Clone #BCH4/#16-1) possess a suitable sensitivity (equal to or less than 0.1 ng/mL) and a suitable dynamic range (0-50 ng/mL) for the measurement of Id3 in mouse and human samples or samples from test systems such as mouse models of human cancer, which evaluate the ability of chemicals to modulate Id3 gene expression or Id3 protein activity.

Example 14

Preparing HRP Conjugate of Rabbit Anti-Human Id3

HRP-conjugated rabbit polyclonal anti-Id3, rabbit monoclonal anti-human Id3, rabbit monoclonal anti-mouse Id3, and rabbit monoclonal anti-mouse/human Id3, are prepared.

Materials
1. The conjugation is performed with rabbit anti-Id3 (polyclonal, affinity purified).
2. HRP is obtained as a powder from Zymed Laboratories, South San Francisco, Calif.
3. S-300 column is hand-packed using gel obtained from Pharmacia.
4. Remaining chemicals and BSA are standard laboratory reagents.

Procedure
1. Dissolve 7.5 mg horseradish peroxidase (HRP) in 1.875 ml distilled water.
2. Add 0.375 ml freshly made 100 mM NaIO$_4$ and stir for 25 minutes at room temperature in the dark.
3. Dialyze the HRP solution at 4° C., for 16~24 hours, in the dark against 1 mM sodium acetate buffer, pH 4.4.
4. Dialyze 5.0 mg/1.25 ml of rabbit polyclonal anti-human Id3 at 4° C., for 16~24 hours, against 0.01 M sodium bicarbonate buffer, pH 9.6.
5. To the dialyzed HRP solution, add 0.075 ml 200 mM carbonate buffer, pH 9.5, and then 5.0 mg/1.25 ml rabbit polyclonal anti-human Id3 in 10 mM carbonate buffer, pH 9.5.
6. Stir for 3 hours at room temperature in the dark.
7. Dialyze the antibody-HRP conjugate, in the dark, against 4,000 ml of 0.05 M potassium phosphate buffer, pH 7.20, containing 0.85% NaCl, at 2-8° C. for 16-24 hours.
8. Purify the antibody-HRP conjugate using an S-300 column (2.5 cm×100 cm).
9. Collect the desired fractions.
10. Add BSA (0.25% w/v) and polyvinylpyrolidone (PVP, 0.25% w/v) to stabilize the conjugate.
11. Store the rabbit anti-human Id3-HRP conjugate at 2-8° C.

Example 15

Determining Equilibrium Association Constant

Biacore Protocol & Experimental Conditions

Antibodies were immobilized on CM5 sensor chips. All SPR (surface plasmon resonance) assays were carried out in a BIACORE 2000 instrument. A mouse monoclonal antibody was used as reference labeled at the 2nd channel (Fc2) of the chip. Rabbit monoclonal anti-human Id3 (BCH-4/#3-3) or Rabbit monoclonal anti-mouse/human Id3 (BCH-4/#6-1, #16-1 and #17-3) was immobilized on the 4th (Fc4) channel. Final conjugation of antibodies on chip surface was 1878 RU for BCH-4/#3-3, BCH-4/#6-1, BCH-4/#16-1, or BCH-3/#17-3. Mouse Id-3 and human Id-3 were applied as mobile analytes. The binding assays were carried out in HBS-P buffer (10 mM HEPES, pH 7.4, containing 150 mM sodium chloride, 0.005% surfactant P-20 detergent and 0.12% glycerol). Kinetics were determined with 8 different analyte concentrations ranging from 3.4 nM to 573 nM. For analyses, 125 µl of analyte were injected (Kinject protocol) at 30 µl/min and the dissociation lasted for 240 seconds at the same flow rate. The surface was regenerated by washing with 50 µl solution of 100 mM glycine and 100 mM of HCl, pH 1.81, at 60 µl/min and the extra cleaning protocol was followed. The kinetic analyses of sensograms were based on the Langmuir (1:1) binding model. Both association rate constant and dissociation rate constants for the interaction of mouse Id-3 and human Id-3 with the immobilized antibodies were determined from the analysis of sensograms using the Biaevaluation software, version 3.0. All binding curves were corrected for background and bulk refractive index contribution by subtraction of the reference flow cells. Models were fitted globally across the data sets. All experiments and analyses were duplicated.

Results

The equilibrium association constant $K_D$ (binding constant) of antibody BCH-4/#3-3 for human Id-3 was calculated as $2.24 \times 10^{11}$. The equilibrium association constant of antibody BCH-4/#6-1 for human Id3 was calculated as $4.13 \times 10^{11}$ and for mouse Id3 was calculated as $5.26 \times 10^8$. The equilibrium association constant of antibody BCH-4/#16-1 for human Id3 was calculated as $1.89 \times 10^{11}$ and for mouse Id3 was calculated as $2.42 \times 10^9$. The equilibrium association constant of antibody BCH-4/#17-3 for human Id3 was calculated as $7.35 \times 10^{10}$ and for mouse Id3 was calculated as $3.32 \times 10^{11}$.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications can be made therein without departing from the scope of the present invention as set forth in the claims. To particularly point out and distinctly claim the subject matter regarded as invention, the following claims conclude the specification

What is claimed is:

1. A rabbit monoclonal antibody that binds to human Id3 protein, wherein said antibody has a binding constant of greater than $1 \times 10^8$/molar, measured with respect to human Id3 protein; and said antibody has no substantial cross-reactivity with Id1, Id2, or Id4 proteins, wherein said antibody comprises a variable light chain sequence of SEQ ID NO: 6 and a variable heavy chain sequence of SEQ ID NO: 8.

2. A rabbit monoclonal antibody that binds to human Id3 protein, wherein said antibody has binding constants of greater than $1 \times 10^8$/molar, measured with respect to human Id3 protein and mouse Id3 protein; and said antibody has no substantial cross-reactivity with Id1, Id2, or Id4 proteins, wherein said antibody comprises a variable light chain sequence selected from the group consisting of SEQ ID NOs: 10, 14, and 22.

3. A rabbit monoclonal antibody that binds to human Id3 protein, wherein said antibody has binding constants of greater than $1 \times 10^8$/molar, measured with respect to human Id3 protein and mouse Id3 protein; and said antibody has no substantial cross-reactivity with Id1, Id2, or Id4 proteins, wherein said antibody comprises a variable heavy chain sequence selected from the group consisting of SEQ ID NOs: 12 and 16.

4. A method of determining the concentration of human Id3 in a liquid sample, comprising the steps of:

reacting a liquid sample with the rabbit monoclonal antibody according to claim 1, 2, or 3, forming an immunocomplex between human Id3 in the sample and the antibody, and determining the amount of immunocomplex formed.

5. The method according to claim 4, wherein said reacting is contacting the sample with a solid-phase support having surface-attached human Id3 molecules in the presence of the antibody labeled with a reporter molecule, wherein said surface-attached human Id3 is effective to compete with human Id3 in the sample for binding to the antibody.

6. A method of determining the concentration of human Id3 in a liquid sample, comprising the steps of:

reacting a liquid sample with a first antibody attached on a solid support and a second antibody in the liquid phase, wherein the first antibody and the second antibody binds to human Id3 at different epitopes;

forming an immunocomplex among human Id3 in the sample, the first antibody, and the second antibody; and determining the amount of immunocomplex formed;

wherein the first antibody or the second antibody is the rabbit monoclonal antibody according to claim 1, 2, or 3.

7. A method of determining the concentration of mouse Id3 in a liquid sample, comprising the steps of:

reacting a liquid sample with the rabbit monoclonal antibody according to claim 2 or 3, forming an immunocomplex between mouse Id3 in the sample and the antibody, and determining the amount of immunocomplex formed.

8. The method according to claim 7, wherein said reacting is contacting the sample with a solid-phase support having surface-attached mouse Id3 molecules in the presence of the antibody labeled with a reporter molecule, wherein said surface-attached mouse Id3 is effective to compete with mouse Id3 in the sample for binding to the antibody.

9. A method of determining the concentration of mouse Id3 in a liquid sample, comprising the steps of:

reacting a liquid sample with a first antibody attached on a solid support and a second antibody in the liquid phase, wherein the first antibody and the second antibody binds to mouse Id3 at different epitopes;

forming an immunocomplex among mouse Id3 in the sample, the first antibody, and the second antibody; and determining the amount of immunocomplex formed;

wherein the first antibody or the second antibody is the rabbit monoclonal antibody according to claim 2 or 3.

10. A method of detecting human or mouse Id3 in a tissue sample by immunohistochemistry, comprising the steps of:

(a) reacting a tissue sample with the rabbit monoclonal antibody according to claim 1, 2, or 3;

(b) forming an immunocomplex between Id3 in the tissue sample and the antibody, and (c) detecting the immunocomplex formed by staining.

11. The method according to claim 10, wherein the immunocomplex is detected by binding to a labeled secondary antibody.

12. A method for detecting human or mouse Id3 in a sample of tissue homogenate or extract, comprising:

(a) applying a sample on gel;

(b) performing gel electrophoresis and separating proteins in the sample by molecular weight;

(c) transferring the proteins out of the gel and onto a membrane;

(d) reacting the membrane with the rabbit monoclonal antibody according to claim 1, 2, or 3; wherein the antibody forms an immunocomplex with Id1 in the sample; and (e) detecting the immunocomplex.

13. The method according to claim 12, wherein the immunocomplex is detected by binding to a labeled secondary antibody.

* * * * *

SEQUENCE LISTING

<160> NUMBER OF SEQ ID NOS: 24

<210> SEQ ID NO 1
<211> LENGTH: 360
<212> TYPE: DNA
<213> ORGANISM: Human

<400> SEQUENCE: 1

```
atgaaggcgc tgagcccggt gcgcggctgc tacgaggcgg tgtgctgcct gtcggaacgc      60
agtctggcca tcgcccgggg ccgagggaag ggcccggcag ctgaggagcc gctgagcttg     120
ctggacgaca tgaaccactg ctactcccgc ctgcgggaac tggtacccgg agtcccgaga     180
ggcactcagc ttagccaggt ggaaatccta cagcgcgtca tcgactacat tctcgacctg     240
caggtagtcc tggccgagcc agcccctgga cccctgatg gcccccacct tcccatccag      300
acagccgagc tcgctccgga acttgtcatc tccaacgaca aaaggagctt ttgccactga    360
```

<210> SEQ ID NO 2

<211> LENGTH: 119
<212> TYPE: PRT
<213> ORGANISM: Human

<400> SEQUENCE: 2

Met Lys Ala Leu Ser Pro Val Arg Gly Cys Tyr Glu Ala Val Cys Cys
1               5                   10                  15

Leu Ser Glu Arg Ser Leu Ala Ile Ala Arg Gly Arg Gly Lys Gly Pro
            20                  25                  30

Ala Ala Glu Glu Pro Leu Ser Leu Leu Asp Asp Met Asn His Cys Tyr
        35                  40                  45

Ser Arg Leu Arg Glu Leu Val Pro Gly Val Pro Arg Gly Thr Gln Leu
    50                  55                  60

Ser Gln Val Glu Ile Leu Gln Arg Val Ile Asp Tyr Ile Leu Asp Leu
65                  70                  75                  80

Gln Val Val Leu Ala Glu Pro Ala Pro Gly Pro Pro Asp Gly Pro His
                85                  90                  95

Leu Pro Ile Gln Thr Ala Glu Leu Ala Pro Glu Leu Val Ile Ser Asn
            100                 105                 110

Asp Lys Arg Ser Phe Cys His
        115

<210> SEQ ID NO 3
<211> LENGTH: 360
<212> TYPE: DNA
<213> ORGANISM: Mouse

<400> SEQUENCE: 3
atgaaggcgc tgagcccggt gcgcggctgc tacgaggcgg tgtgctgcct gtcggaacgt      60
agcctggcca ttgcgcgagg ccgcggtaag agcccgtcga ccgaggagcc tcttagcctc     120
ttggacgaca tgaaccactg ctactcgcgc ctgcgggaac tggtgccggg agtcccgcga     180
ggcactcagc ttagccaggt ggaaatcctg cagcgtgtca tagactacat cctcgacctt     240
caggtggtcc tggcagagcc ggcgcctgga ccccccggacg tccgcatct cccgatccag     300 acagctgagc tcactccgga acttgtgatc tccaaggaca agaggagctt tgccactga     360

<210> SEQ ID NO 4
<211> LENGTH: 119
<212> TYPE: PRT
<213> ORGANISM: Mouse

<400> SEQUENCE: 4

Met Lys Ala Leu Ser Pro Val Arg Gly Cys Tyr Glu Ala Val Cys Cys
1               5                   10                  15

Leu Ser Glu Arg Ser Leu Ala Ile Ala Arg Gly Arg Gly Lys Ser Pro
            20                  25                  30

Ser Thr Glu Glu Pro Leu Ser Leu Leu Asp Asp Met Asn His Cys Tyr
        35                  40                  45

Ser Arg Leu Arg Glu Leu Val Pro Gly Val Pro Arg Gly Thr Gln Leu
    50                  55                  60

Ser Gln Val Glu Ile Leu Gln Arg Val Ile Asp Tyr Ile Leu Asp Leu
65                  70                  75                  80

Gln Val Val Leu Ala Glu Pro Ala Pro Gly Pro Pro Asp Gly Pro His
                85                  90                  95

Leu Pro Ile Gln Thr Ala Glu Leu Thr Pro Glu Leu Val Ile Ser Lys
            100                 105                 110

Asp Lys Arg Ser Phe Cys His
        115

<210> SEQ ID NO 5
<211> LENGTH: 327
<212> TYPE: DNA
<213> ORGANISM: Rabbit
<220> FEATURE:
<221> NAME/KEY: CDS
<222> LOCATION: (1)..(327)

<400> SEQUENCE: 5

```
caa gtg ctg acc cag act cca tct ccc gtg tct gca gct gtg gga ggc      48
Gln Val Leu Thr Gln Thr Pro Ser Pro Val Ser Ala Ala Val Gly Gly
1               5                   10                  15 aca gtc acc atc aat tgc cag gcc agt cag agt att tat aat gac aac      96
Thr Val Thr Ile Asn Cys Gln Ala Ser Gln Ser Ile Tyr Asn Asp Asn
            20                  25                  30 gac tta gct tgg ttt cag cag aaa cca ggg cag cct ccc aag ctc ctg     144
Asp Leu Ala Trp Phe Gln Gln Lys Pro Gly Gln Pro Pro Lys Leu Leu
        35                  40                  45 atc tat gat gca tcc act ctg aca tct ggg gtc cca tcg cgg ttc aaa     192
Ile Tyr Asp Ala Ser Thr Leu Thr Ser Gly Val Pro Ser Arg Phe Lys
    50                  55                  60 ggc agt gga tct ggg aca caa ttc act ctc acc atc agc gac ctg gac     240
Gly Ser Gly Ser Gly Thr Gln Phe Thr Leu Thr Ile Ser Asp Leu Asp
65                  70                  75                  80 tgt gac gat gct gcc act tac tac tgt gca gcc cgt tat agt ggt aat     288
Cys Asp Asp Ala Ala Thr Tyr Tyr Cys Ala Ala Arg Tyr Ser Gly Asn
                85                  90                  95 att tat ggt ttc ggc gga ggg acc gag gtg gtg gtc aaa                 327
Ile Tyr Gly Phe Gly Gly Gly Thr Glu Val Val Val Lys
                100                 105
```

<210> SEQ ID NO 6
<211> LENGTH: 109
<212> TYPE: PRT
<213> ORGANISM: Rabbit

<400> SEQUENCE: 6

Gln Val Leu Thr Gln Thr Pro Ser Pro Val Ser Ala Ala Val Gly Gly
1               5                   10                  15

Thr Val Thr Ile Asn Cys Gln Ala Ser Gln Ser Ile Tyr Asn Asp Asn
            20                  25                  30

Asp Leu Ala Trp Phe Gln Gln Lys Pro Gly Gln Pro Pro Lys Leu Leu
        35                  40                  45

Ile Tyr Asp Ala Ser Thr Leu Thr Ser Gly Val Pro Ser Arg Phe Lys
    50                  55                  60

Gly Ser Gly Ser Gly Thr Gln Phe Thr Leu Thr Ile Ser Asp Leu Asp
65                  70                  75                  80

Cys Asp Asp Ala Ala Thr Tyr Tyr Cys Ala Ala Arg Tyr Ser Gly Asn
                85                  90                  95

Ile Tyr Gly Phe Gly Gly Gly Thr Glu Val Val Val Lys
                100                 105

<210> SEQ ID NO 7
<211> LENGTH: 336
<212> TYPE: DNA
<213> ORGANISM: Rabbit
<220> FEATURE:
<221> NAME/KEY: CDS
<222> LOCATION: (1)..(336)

<400> SEQUENCE: 7

```
cag tcg gtg gag gag tcc ggg ggt cgc ctg gtc acg cct ggg aca ccc      48
Gln Ser Val Glu Glu Ser Gly Gly Arg Leu Val Thr Pro Gly Thr Pro
1               5                   10                  15 ctg aca ctc acc tgc aca gtc tct gga atc gac ctc agt agc tat gca      96
Leu Thr Leu Thr Cys Thr Val Ser Gly Ile Asp Leu Ser Ser Tyr Ala
            20                  25                  30 atg agc tgg gtc cgc cag gct cca ggg aag ggg ctg gaa tgg atc gga     144
Met Ser Trp Val Arg Gln Ala Pro Gly Lys Gly Leu Glu Trp Ile Gly
        35                  40                  45 gtc att ttt cct agt aat aat gta tat tac gcg agc tgg gcg aaa ggc     192
Val Ile Phe Pro Ser Asn Asn Val Tyr Tyr Ala Ser Trp Ala Lys Gly
    50                  55                  60 cga ttc acc atc tcc aaa acc tcg acc acg gtg gat ctg aaa atc acc     240
Arg Phe Thr Ile Ser Lys Thr Ser Thr Thr Val Asp Leu Lys Ile Thr
65                  70                  75                  80 agt ccg aca acc gag gac acg gcc acc tat ttc tgt gcc agt atg ggt     288
Ser Pro Thr Thr Glu Asp Thr Ala Thr Tyr Phe Cys Ala Ser Met Gly
                85                  90                  95 gct ttt gat tcc tgg ggc cca ggc acc ctg gtc acc gtc tcc tca ggg     336
Ala Phe Asp Ser Trp Gly Pro Gly Thr Leu Val Thr Val Ser Ser Gly
            100                 105                 110
```

<210> SEQ ID NO 8
<211> LENGTH: 112
<212> TYPE: PRT
<213> ORGANISM: Rabbit

<400> SEQUENCE: 8

```
Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Tyr Ala
            20                  25                  30

Met Ser Trp Val Arg Gln Ala Pro Gly Lys Gly Leu Glu Trp Ile Gly
        35                  40                  45

Val Ile Phe Pro Ser Asn Asn Val Tyr Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Ser Met Gly
                85                  90                  95

Ala Phe Asp Ser Trp Gly Pro Gly Thr Leu Val Thr Val Ser Ser Gly
            100                 105                 110
```

<210> SEQ ID NO 9
<211> LENGTH: 333
<212> TYPE: DNA
<213> ORGANISM: Rabbit
<220> FEATURE:
<221> NAME/KEY: CDS
<222> LOCATION: (1)..(333)

<400> SEQUENCE: 9

```
gcc gtg ctg acc cag act cca tct ccc gtg tct gca gct gtg gga ggc      48
Ala Val Leu Thr Gln Thr Pro Ser Pro Val Ser Ala Ala Val Gly Gly
1               5                   10                  15 aca gtc agc att agt tgc cag tcc agt cag agt gtt tgg aat aac aac      96
Thr Val Ser Ile Ser Cys Gln Ser Ser Gln Ser Val Trp Asn Asn Asn
            20                  25                  30
```

```
tgg tta tcc tgg ttt cag cag aaa cca ggg cag cct ccc aag ctc ctg      144
Trp Leu Ser Trp Phe Gln Gln Lys Pro Gly Gln Pro Pro Lys Leu Leu
        35                  40                  45 atc tat gaa aca tcc aaa ctg gaa tct ggg gtc cca tcg cgg ttc aaa      192
Ile Tyr Glu Thr Ser Lys Leu Glu Ser Gly Val Pro Ser Arg Phe Lys
 50                  55                  60 ggc agt gga tct ggg aca cag ttc act ctc acc atc agc gac gtg cag      240
Gly Ser Gly Ser Gly Thr Gln Phe Thr Leu Thr Ile Ser Asp Val Gln
 65                  70                  75                  80 tgt gac gat gct gcc act tac tac tgt cta ggc ggt tat tgg act act      288
Cys Asp Asp Ala Ala Thr Tyr Tyr Cys Leu Gly Gly Tyr Trp Thr Thr
                 85                  90                  95 agt gat aat aat gtt ttc ggc gga ggg acc gag gtg gtg gtc aaa          333
Ser Asp Asn Asn Val Phe Gly Gly Gly Thr Glu Val Val Val Lys
            100                 105                 110

<210> SEQ ID NO 10
<211> LENGTH: 111
<212> TYPE: PRT
<213> ORGANISM: Rabbit

<400> SEQUENCE: 10

Ala Val Leu Thr Gln Thr Pro Ser Pro Val Ser Ala Ala Val Gly Gly
 1               5                  10                  15

Thr Val Ser Ile Ser Cys Gln Ser Ser Gln Ser Val Trp Asn Asn Asn
            20                  25                  30

Trp Leu Ser Trp Phe Gln Gln Lys Pro Gly Gln Pro Pro Lys Leu Leu
        35                  40                  45

Ile Tyr Glu Thr Ser Lys Leu Glu Ser Gly Val Pro Ser Arg Phe Lys
 50                  55                  60

Gly Ser Gly Ser Gly Thr Gln Phe Thr Leu Thr Ile Ser Asp Val Gln
 65                  70                  75                  80

Cys Asp Asp Ala Ala Thr Tyr Tyr Cys Leu Gly Gly Tyr Trp Thr Thr
                 85                  90                  95

Ser Asp Asn Asn Val Phe Gly Gly Gly Thr Glu Val Val Val Lys
            100                 105                 110

<210> SEQ ID NO 11
<211> LENGTH: 333
<212> TYPE: DNA
<213> ORGANISM: Rabbit
<220> FEATURE:
<221> NAME/KEY: CDS
<222> LOCATION: (1)..(333)

<400> SEQUENCE: 11 cag tcg gtg gag gag tcc ggc ggt cgc ctg gtc acg cct ggg aca ccc       48
Gln Ser Val Glu Glu Ser Gly Gly Arg Leu Val Thr Pro Gly Thr Pro
 1               5                  10                  15 ctg aca ctc acc tgc aca gcc tct gga ttc tcc ctc agt aat gtc tac       96
Leu Thr Leu Thr Cys Thr Ala Ser Gly Phe Ser Leu Ser Asn Val Tyr
            20                  25                  30 ata cac tgg gtc cgc cag gct cca ggg aag ggg ctg gaa tgg atc gga      144
Ile His Trp Val Arg Gln Ala Pro Gly Lys Gly Leu Glu Trp Ile Gly
        35                  40                  45 tac att agt gat ggt gat act gca cgc tac gcg acc tgg gcg aaa ggc      192
Tyr Ile Ser Asp Gly Asp Thr Ala Arg Tyr Ala Thr Trp Ala Lys Gly
 50                  55                  60 cga ttc acc atc tcc aaa acc tcg tcg acc acg gtg aat ctg aaa atg      240
Arg Phe Thr Ile Ser Lys Thr Ser Ser Thr Thr Val Asn Leu Lys Met
 65                  70                  75                  80
```

```
acc agt ctg aca acc gag gac acg gcc acc tat ttt tgt gcc aga cag      288
Thr Ser Leu Thr Thr Glu Asp Thr Ala Thr Tyr Phe Cys Ala Arg Gln
            85                  90                  95 gga ttt aac atc tgg ggc cca ggc acc ctg gtc acc gtc tcc tta          333
Gly Phe Asn Ile Trp Gly Pro Gly Thr Leu Val Thr Val Ser Leu
        100                 105                 110

<210> SEQ ID NO 12
<211> LENGTH: 111
<212> TYPE: PRT
<213> ORGANISM: Rabbit

<400> SEQUENCE: 12

Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Ser Asn Val Tyr
            20                  25                  30

Ile His Trp Val Arg Gln Ala Pro Gly Lys Gly Leu Glu Trp Ile Gly
        35                  40                  45

Tyr Ile Ser Asp Gly Asp Thr Ala Arg Tyr Ala Thr Trp Ala Lys Gly
    50                  55                  60

Arg Phe Thr Ile Ser Lys Thr Ser Thr Thr Val Asn Leu Lys Met
65                  70                  75                  80

Thr Ser Leu Thr Thr Glu Asp Thr Ala Thr Tyr Phe Cys Ala Arg Gln
            85                  90                  95

Gly Phe Asn Ile Trp Gly Pro Gly Thr Leu Val Thr Val Ser Leu
        100                 105                 110

<210> SEQ ID NO 13
<211> LENGTH: 333
<212> TYPE: DNA
<213> ORGANISM: Rabbit
<220> FEATURE:
<221> NAME/KEY: CDS
<222> LOCATION: (1)..(333)

<400> SEQUENCE: 13 gcc gtg ctg acc cag act cca tct ccc gtg tct gca gct gtg gga ggc      48
Ala Val Leu Thr Gln Thr Pro Ser Pro Val Ser Ala Ala Val Gly Gly
1               5                   10                  15 aca gtc acc att agt tgc cag tcc agt cag agt gtt tat aat aac aac      96
Thr Val Thr Ile Ser Cys Gln Ser Ser Gln Ser Val Tyr Asn Asn Asn
            20                  25                  30 tgg tta tcc tgg ttt cag cag aaa tca ggg cag cct ccc aag ctc ctg      144
Trp Leu Ser Trp Phe Gln Gln Lys Ser Gly Gln Pro Pro Lys Leu Leu
        35                  40                  45 atc tat gaa aca tcc aaa ctg gaa tct ggg gtc cca tcg cgg ttc aaa      192
Ile Tyr Glu Thr Ser Lys Leu Glu Ser Gly Val Pro Ser Arg Phe Lys
    50                  55                  60 ggc agt gga tct ggg aca cag ttc act ctc acc atc atc gac gtg cag      240
Gly Ser Gly Ser Gly Thr Gln Phe Thr Leu Thr Ile Ile Asp Val Gln
65                  70                  75                  80 tgt gac gat gct gcc act tac tac tgt cta ggc ggt tat tgg act act      288
Cys Asp Asp Ala Ala Thr Tyr Tyr Cys Leu Gly Gly Tyr Trp Thr Thr
            85                  90                  95 agt gat aat aat att ttc ggc gga ggg acc gag gtg gtg gtc aaa          333
Ser Asp Asn Asn Ile Phe Gly Gly Gly Thr Glu Val Val Val Lys
        100                 105                 110

<210> SEQ ID NO 14
```

<211> LENGTH: 111
<212> TYPE: PRT
<213> ORGANISM: Rabbit

<400> SEQUENCE: 14

Ala Val Leu Thr Gln Thr Pro Ser Pro Val Ser Ala Ala Val Gly Gly
1               5                   10                  15

Thr Val Thr Ile Ser Cys Gln Ser Ser Gln Ser Val Tyr Asn Asn Asn
            20                  25                  30

Trp Leu Ser Trp Phe Gln Gln Lys Ser Gly Gln Pro Pro Lys Leu Leu
        35                  40                  45

Ile Tyr Glu Thr Ser Lys Leu Glu Ser Gly Val Pro Ser Arg Phe Lys
    50                  55                  60

Gly Ser Gly Ser Gly Thr Gln Phe Thr Leu Thr Ile Ile Asp Val Gln
65                  70                  75                  80

Cys Asp Asp Ala Ala Thr Tyr Tyr Cys Leu Gly Gly Tyr Trp Thr Thr
                85                  90                  95

Ser Asp Asn Asn Ile Phe Gly Gly Gly Thr Glu Val Val Val Lys
            100                 105                 110

<210> SEQ ID NO 15
<211> LENGTH: 333
<212> TYPE: DNA
<213> ORGANISM: Rabbit
<220> FEATURE:
<221> NAME/KEY: CDS
<222> LOCATION: (1)..(333)

<400> SEQUENCE: 15 cag tcg gtg gag gag tcc ggc ggt cgc ctg gtc acg cct ggg aca ccc       48
Gln Ser Val Glu Glu Ser Gly Gly Arg Leu Val Thr Pro Gly Thr Pro
1               5                   10                  15 ctg aca ctc acc tgc aca gcc tct gga ttc tcc ctc agt agc tac tac       96
Leu Thr Leu Thr Cys Thr Ala Ser Gly Phe Ser Leu Ser Ser Tyr Tyr
            20                  25                  30 ata cac tgg gtc cgc cag gct cca ggg aag gcg ctg gaa tgg atc gga      144
Ile His Trp Val Arg Gln Ala Pro Gly Lys Ala Leu Glu Trp Ile Gly
        35                  40                  45 tat att agt gat ggt ggg act aca tac tac gcg agc tgg gcg aaa ggc      192
Tyr Ile Ser Asp Gly Gly Thr Thr Tyr Tyr Ala Ser Trp Ala Lys Gly
    50                  55                  60 cga ttc acc atc tcc aaa acc tcg tcg acc acg gtg gat ctg aaa atg      240
Arg Phe Thr Ile Ser Lys Thr Ser Ser Thr Thr Val Asp Leu Lys Met
65                  70                  75                  80 acc agt ctg aca acc gag gac acg gcc acc tat ttt tgt gcc aga cag      288
Thr Ser Leu Thr Thr Glu Asp Thr Ala Thr Tyr Phe Cys Ala Arg Gln
                85                  90                  95 gga ttt aac atc tgg ggc cca ggc acc ctg gtc acc gtc tcc tta           333
Gly Phe Asn Ile Trp Gly Pro Gly Thr Leu Val Thr Val Ser Leu
            100                 105                 110

<210> SEQ ID NO 16
<211> LENGTH: 111
<212> TYPE: PRT
<213> ORGANISM: Rabbit

<400> SEQUENCE: 16

Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr Tyr
            20                  25                  30

Ile His Trp Val Arg Gln Ala Pro Gly Lys Ala Leu Glu Trp Ile Gly
           35                  40                  45

Tyr Ile Ser Asp Gly Gly Thr Thr Tyr Tyr Ala Ser Trp Ala Lys Gly
       50                  55                  60

Arg Phe Thr Ile Ser Lys Thr Ser Ser Thr Thr Val Asp Leu Lys Met
65                  70                  75                  80

Thr Ser Leu Thr Thr Glu Asp Thr Ala Thr Tyr Phe Cys Ala Arg Gln
               85                   90                  95

Gly Phe Asn Ile Trp Gly Pro Gly Thr Leu Val Thr Val Ser Leu
               100                 105                 110

<210> SEQ ID NO 17
<211> LENGTH: 333
<212> TYPE: DNA
<213> ORGANISM: Rabbit
<220> FEATURE:
<221> NAME/KEY: CDS
<222> LOCATION: (1)..(333)

<400> SEQUENCE: 17 gcc gtg ctg acc cag act cca tct ccc gtg tct gca gct gtg gga ggc     48
Ala Val Leu Thr Gln Thr Pro Ser Pro Val Ser Ala Ala Val Gly Gly
1               5                   10                  15 aca gtc agc att agt tgc cag tcc agt cag agt gtt tgg aat aac aac     96
Thr Val Ser Ile Ser Cys Gln Ser Ser Gln Ser Val Trp Asn Asn Asn
           20                   25                  30 tgg tta tcc tgg ttt cag cag aaa cca ggg cag cct ccc aag ctc ctg    144
Trp Leu Ser Trp Phe Gln Gln Lys Pro Gly Gln Pro Pro Lys Leu Leu
       35                  40                  45 atc tat gaa aca tcc aaa ctg gaa tct ggg gtc cca tcg cgg ttc aaa    192
Ile Tyr Glu Thr Ser Lys Leu Glu Ser Gly Val Pro Ser Arg Phe Lys
   50                  55                  60 ggc agt gga tct ggg aca cag ttc act ctc acc atc agc gac gtg cag    240
Gly Ser Gly Ser Gly Thr Gln Phe Thr Leu Thr Ile Ser Asp Val Gln
65                  70                  75                  80 tgt gac gat gct gcc act tac tac tgt cta ggc ggt tat tgg act act    288
Cys Asp Asp Ala Ala Thr Tyr Tyr Cys Leu Gly Gly Tyr Trp Thr Thr
               85                  90                  95 agt gat aat aat gtt ttc ggc gga ggg acc gag gtg gtg gtc aaa        333
Ser Asp Asn Asn Val Phe Gly Gly Gly Thr Glu Val Val Val Lys
               100                 105                 110

<210> SEQ ID NO 18
<211> LENGTH: 111
<212> TYPE: PRT
<213> ORGANISM: Rabbit

<400> SEQUENCE: 18

Ala Val Leu Thr Gln Thr Pro Ser Pro Val Ser Ala Ala Val Gly Gly
1               5                   10                  15

Thr Val Ser Ile Ser Cys Gln Ser Ser Gln Ser Val Trp Asn Asn Asn
           20                   25                  30

Trp Leu Ser Trp Phe Gln Gln Lys Pro Gly Gln Pro Pro Lys Leu Leu
       35                  40                  45

Ile Tyr Glu Thr Ser Lys Leu Glu Ser Gly Val Pro Ser Arg Phe Lys
   50                  55                  60

Gly Ser Gly Ser Gly Thr Gln Phe Thr Leu Thr Ile Ser Asp Val Gln
65                  70                  75                  80

Cys Asp Asp Ala Ala Thr Tyr Tyr Cys Leu Gly Gly Tyr Trp Thr Thr

```
                        85                  90                  95
Ser Asp Asn Asn Val Phe Gly Gly Gly Thr Glu Val Val Lys
                100                 105                 110

<210> SEQ ID NO 19
<211> LENGTH: 333
<212> TYPE: DNA
<213> ORGANISM: Rabbit
<220> FEATURE:
<221> NAME/KEY: CDS
<222> LOCATION: (1)..(333)

<400> SEQUENCE: 19 cag tcg gtg gag gag tcc ggc ggt cgc ctg gtc acg cct ggg aca ccc       48
Gln Ser Val Glu Glu Ser Gly Gly Arg Leu Val Thr Pro Gly Thr Pro
1               5                   10                  15 ctg aca ctc acc tgc aca gcc tct gga ttc tcc ctc agt aat gtc tac       96
Leu Thr Leu Thr Cys Thr Ala Ser Gly Phe Ser Leu Ser Asn Val Tyr
            20                  25                  30 ata cac tgg gtc cgc cag gct cca ggg aag ggg ctg gaa tgg atc gga      144
Ile His Trp Val Arg Gln Ala Pro Gly Lys Gly Leu Glu Trp Ile Gly
        35                  40                  45 tac att agt gat ggt gat act gca cgc tac gcg acc tgg gcg aaa ggc      192
Tyr Ile Ser Asp Gly Asp Thr Ala Arg Tyr Ala Thr Trp Ala Lys Gly
    50                  55                  60 cga ttc acc atc tcc aaa acc tcg tcg acc acg gtg aat ctg aaa atg      240
Arg Phe Thr Ile Ser Lys Thr Ser Ser Thr Thr Val Asn Leu Lys Met
65                  70                  75                  80 acc agt ctg aca acc gag gac acg gcc acc tat ttt tgt gcc aga cag      288
Thr Ser Leu Thr Thr Glu Asp Thr Ala Thr Tyr Phe Cys Ala Arg Gln
                85                  90                  95 gga ttt aac atc tgg ggc cca ggc acc ctg gtc acc gtc tcc tta          333
Gly Phe Asn Ile Trp Gly Pro Gly Thr Leu Val Thr Val Ser Leu
            100                 105                 110

<210> SEQ ID NO 20
<211> LENGTH: 111
<212> TYPE: PRT
<213> ORGANISM: Rabbit

<400> SEQUENCE: 20

Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Ser Asn Val Tyr
            20                  25                  30

Ile His Trp Val Arg Gln Ala Pro Gly Lys Gly Leu Glu Trp Ile Gly
        35                  40                  45

Tyr Ile Ser Asp Gly Asp Thr Ala Arg Tyr Ala Thr Trp Ala Lys Gly
    50                  55                  60

Arg Phe Thr Ile Ser Lys Thr Ser Ser Thr Thr Val Asn Leu Lys Met
65                  70                  75                  80

Thr Ser Leu Thr Thr Glu Asp Thr Ala Thr Tyr Phe Cys Ala Arg Gln
                85                  90                  95

Gly Phe Asn Ile Trp Gly Pro Gly Thr Leu Val Thr Val Ser Leu
            100                 105                 110

<210> SEQ ID NO 21
<211> LENGTH: 333
<212> TYPE: DNA
<213> ORGANISM: Rabbit
<220> FEATURE:
```

<210> SEQ ID NO 21 continues...

```
<221> NAME/KEY: CDS
<222> LOCATION: (1)..(333)

<400> SEQUENCE: 21 gcc gtg ctg acc cag act cca tct ccc gtg tct gca gct gtg gga ggc      48
Ala Val Leu Thr Gln Thr Pro Ser Pro Val Ser Ala Ala Val Gly Gly
1               5                   10                  15 aca gtc acc atc agt tgc cag tcc agt cag agt gtt tat aat aac aac      96
Thr Val Thr Ile Ser Cys Gln Ser Ser Gln Ser Val Tyr Asn Asn Asn
            20                  25                  30 tgg tta tcc tgg ttt cag cag aaa tca ggg cag cct ccc aag ctc ctg     144
Trp Leu Ser Trp Phe Gln Gln Lys Ser Gly Gln Pro Pro Lys Leu Leu
        35                  40                  45 atc tac gaa aca tcc aaa ctg gaa tct ggg gtc cca tcg cgg ttc aaa     192
Ile Tyr Glu Thr Ser Lys Leu Glu Ser Gly Val Pro Ser Arg Phe Lys
    50                  55                  60 ggc agt gga tct ggg aca cag ttc act ctc acc atc atc gac gtg cag     240
Gly Ser Gly Ser Gly Thr Gln Phe Thr Leu Thr Ile Ile Asp Val Gln
65                  70                  75                  80 tgt gac gat gct gcc act tac tac tgt cta ggc ggt tat tgg agt act     288
Cys Asp Asp Ala Ala Thr Tyr Tyr Cys Leu Gly Gly Tyr Trp Ser Thr
                85                  90                  95 agt gat aat aat att ttc ggc gga ggg acc gag gtg gtg gtc aaa         333
Ser Asp Asn Asn Ile Phe Gly Gly Gly Thr Glu Val Val Val Lys
            100                 105                 110

<210> SEQ ID NO 22
<211> LENGTH: 111
<212> TYPE: PRT
<213> ORGANISM: Rabbit

<400> SEQUENCE: 22

Ala Val Leu Thr Gln Thr Pro Ser Pro Val Ser Ala Ala Val Gly Gly
1               5                   10                  15

Thr Val Thr Ile Ser Cys Gln Ser Ser Gln Ser Val Tyr Asn Asn Asn
            20                  25                  30

Trp Leu Ser Trp Phe Gln Gln Lys Ser Gly Gln Pro Pro Lys Leu Leu
        35                  40                  45

Ile Tyr Glu Thr Ser Lys Leu Glu Ser Gly Val Pro Ser Arg Phe Lys
    50                  55                  60

Gly Ser Gly Ser Gly Thr Gln Phe Thr Leu Thr Ile Ile Asp Val Gln
65                  70                  75                  80

Cys Asp Asp Ala Ala Thr Tyr Tyr Cys Leu Gly Gly Tyr Trp Ser Thr
                85                  90                  95

Ser Asp Asn Asn Ile Phe Gly Gly Gly Thr Glu Val Val Val Lys
            100                 105                 110

<210> SEQ ID NO 23
<211> LENGTH: 333
<212> TYPE: DNA
<213> ORGANISM: Rabbit
<220> FEATURE:
<221> NAME/KEY: CDS
<222> LOCATION: (1)..(333)

<400> SEQUENCE: 23 cag tcg gtg gag gag tcc ggc ggt cgc ctg gtc acg cct ggg aca ccc      48
Gln Ser Val Glu Glu Ser Gly Gly Arg Leu Val Thr Pro Gly Thr Pro
1               5                   10                  15 ctg aca ctc acc tgc aca gcc tct gga ttc tcc ctc agt agc tac tac      96
Leu Thr Leu Thr Cys Thr Ala Ser Gly Phe Ser Leu Ser Ser Tyr Tyr
            20                  25                  30
```

-continued

```
              20                  25                  30
ata cac tgg gtc cgc cag gct cca ggg aag gcg ctg gaa tgg atc gga    144
Ile His Trp Val Arg Gln Ala Pro Gly Lys Ala Leu Glu Trp Ile Gly
        35                  40                  45 tat att agt gat ggt ggg act aca tac tac gcg agc tgg gcg aaa ggc    192
Tyr Ile Ser Asp Gly Gly Thr Thr Tyr Tyr Ala Ser Trp Ala Lys Gly
    50                  55                  60 cga ttc acc atc tcc aaa acc tcg tcg acc acg gtg gat ctg aaa atg    240
Arg Phe Thr Ile Ser Lys Thr Ser Ser Thr Thr Val Asp Leu Lys Met
65                  70                  75                  80 acc agt ctg aca acc gag gac acg gcc acc tat ttt tgt gcc aga cag    288
Thr Ser Leu Thr Thr Glu Asp Thr Ala Thr Tyr Phe Cys Ala Arg Gln
                85                  90                  95 gga ttt aac atc tgg ggc cca ggc acc ctg gtc acc gtc tcc tta        333
Gly Phe Asn Ile Trp Gly Pro Gly Thr Leu Val Thr Val Ser Leu
            100                 105                 110
```

<210> SEQ ID NO 24
<211> LENGTH: 111
<212> TYPE: PRT
<213> ORGANISM: Rabbit

<400> SEQUENCE: 24

```
Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr Tyr
            20                  25                  30

Ile His Trp Val Arg Gln Ala Pro Gly Lys Ala Leu Glu Trp Ile Gly
        35                  40                  45

Tyr Ile Ser Asp Gly Gly Thr Thr Tyr Tyr Ala Ser Trp Ala Lys Gly
    50                  55                  60

Arg Phe Thr Ile Ser Lys Thr Ser Ser Thr Thr Val Asp Leu Lys Met
65                  70                  75                  80

Thr Ser Leu Thr Thr Glu Asp Thr Ala Thr Tyr Phe Cys Ala Arg Gln
                85                  90                  95

Gly Phe Asn Ile Trp Gly Pro Gly Thr Leu Val Thr Val Ser Leu
            100                 105                 110
```